United States Patent [19]
Petrie et al.

[11] Patent Number: 5,824,796
[45] Date of Patent: Oct. 20, 1998

[54] CROSS-LINKING OLIGONUCLEOTIDES

[75] Inventors: Charles R. Petrie; Rich B. Meyer, both of Woodinville; John C. Tabone, Bothell, all of Wash.; Gerald D. Hurst, Iowa City, Iowa

[73] Assignee: EPOCH Pharmaceuticals, Inc., Bothell, Wash.

[21] Appl. No.: 334,490

[22] Filed: Nov. 4, 1994

Related U.S. Application Data

[63] Continuation of Ser. No. 49,807, Apr. 20, 1993, abandoned, which is a continuation of Ser. No. 353,857, May 18, 1989, abandoned, which is a continuation-in-part of Ser. No. 250,474, Sep. 28, 1988, abandoned.

[51] Int. Cl.[6] .......................... C07H 19/04; C07H 21/00; C07H 21/02; C07H 21/04
[52] U.S. Cl. .......................................... 536/26.7; 536/24.5
[58] Field of Search ................................ 536/26.1, 26.12, 536/26.13, 26.14, 26.8, 27.6, 27.81, 28.5, 28.54, 26.7, 24.5

[56] References Cited

U.S. PATENT DOCUMENTS

| | | | |
|---|---|---|---|
| 3,598,807 | 8/1971 | Nakayama et al. | |
| 3,962,211 | 6/1976 | Townsend et al. | |
| 4,123,610 | 10/1978 | Summerton et al. | 536/28 |
| 4,582,789 | 4/1986 | Sheldon et al. | |
| 4,599,303 | 7/1986 | Yabusaki et al. | |
| 4,711,955 | 12/1987 | Ward et al. | 536/29 |
| 4,766,062 | 8/1988 | Diamond et al. | 435/6 |
| 4,795,700 | 1/1989 | Dervan et al. | |
| 4,837,311 | 6/1989 | Tam et al. | |
| 5,176,996 | 1/1993 | Hogan et al. | 436/6 |

FOREIGN PATENT DOCUMENTS

| | | | |
|---|---|---|---|
| 0021293 | 1/1981 | European Pat. Off. | |
| 0198207 | 10/1986 | European Pat. Off. | C12Q 1/68 |
| 0227459 | 7/1987 | European Pat. Off. | |
| 0242264 | 10/1987 | European Pat. Off. | C12P 19/34 |
| 0259186 | 3/1988 | European Pat. Off. | |
| 0266099 | 5/1988 | European Pat. Off. | C07H 21/04 |
| 0267996 | 5/1988 | European Pat. Off. | |
| 0375406 | 6/1990 | European Pat. Off. | C12N 15/10 |
| 3310337 | 9/1984 | Germany | |
| 6109797 | 11/1984 | Japan | |
| 84/03285 | 8/1984 | WIPO | C07H 17/00 |
| WO8502628 | 6/1985 | WIPO | |
| WO8503075 | 7/1985 | WIPO | |
| 86/02929 | 5/1986 | WIPO | C07H 15/12 |
| 86/04816 | 8/1986 | WIPO | A61K 31/70 |
| WO8707611 | 12/1987 | WIPO | |
| 88/10264 | 12/1988 | WIPO | C07H 19/10 |
| 90/14353 | 11/1990 | WIPO | C07H 21/00 |
| 90/15884 | 12/1990 | WIPO | C12Q 1/68 |
| 91/18997 | 12/1991 | WIPO | C12P 19/34 |
| 92/20698 | 11/1992 | WIPO | C07H 21/04 |
| 93/03736 | 3/1993 | WIPO | A61K 31/70 |

OTHER PUBLICATIONS

Hobbs, Frank W. Jr. *Org. Chem.*, (1989) 54:3420–3422.
Umlauf, Scott W. et al. *J. of Bio. Chem.* (1990) 265/28:16898–16912.
Register, James C. III et al. *J. of Bio. Chem.* (1987) 262/26:12812–12820.
Thoung, Nguyen Thanh et al. *Biochimie*, (1985) 67:673–684.
Chang, Susanne et al. *J. of Bio. Chem.* (1988) 263/20:15110–15117.
Knorre, D. G. et al. "complementarily addressed modification of double–stranded DNA in a triple–stranded complex" *Dokl. Akad. NAUK SSSR* (1988) 300/4:1006–9.
Petrie, Charles T. et al. *Bioconjugate Chemistry*, (1991) 2/6:441–446.
Sidwell, Robert W. et al. *Applied Microbiology*, (1968) 16/2:370–392.
Seela, Frank et al. *Nucleic Acids Research*, (1982) 10/4:1389–1397.

(List continued on next page.)

*Primary Examiner*—Gary L. Kunz
*Attorney, Agent, or Firm*—Klein & Szekeres, LLP

[57] ABSTRACT

This invention is directed to novel substituted nucleotide bases with a crosslinking arm which accomplish crosslinking between specific sites on adjoining strands of oligonucleotides or oligodeoxynucleotides. The invention is also directed to oligonucleotides comprising at least one of these crosslinking agents and to the use of the resulting novel oligonucleotides for diagnostic and therapeutic purposes. The crosslinking agents of the invention are of the following formula (I'):

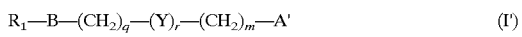

$$R_1-B-(CH_2)_q-(Y)_r-(CH_2)_m-A' \qquad (I')$$

wherein, $R_1$ is hydrogen, or a sugar moiety or analog thereof optionally substituted at its 3' or its 5' position with a phosphorus derivative attached to the sugar moiety by an oxygen and including groups $Q_1$ $Q_2$ and $Q_3$ or with a reactive precursor thereof suitable for nucleotide bond formation;

$Q_1$ is hydroxy, phosphate or diphosphate;

$Q_2$ is =O or =S;

$Q_3$ is $CH_2$—R', S—R', O—R', or N—R'R";

each of R' and R" is independently hydrogen or $C_{1-6}$ alkyl;

B is a nucleic acid base or analog thereof that is a component of an oligonucleotide;

Y is a functional linking group;

each of m and q is independently 0 to 8, inclusive;

r is 0 or 1; and

A' is a leaving group.

This invention is also directed to novel 3,4-disubstituted and 3,4,-trisubstituted pyrazolo[3,4-d]-pyrimidines and to the use of these nucleic acid bases in the preparation of oligonucleotides. The invention includes nucleosides and mono- and oligonucleotides comprising at least one of these pyrazolopyrimidines, and to the use of the resulting novel oligonucleotides for diagnostic purposes.

15 Claims, 3 Drawing Sheets

OTHER PUBLICATIONS

Elsner, Henrik et al. *Analytical Biochemistry*, (1985) 149/2:575–581.
Sonenberg, Nahum et al. *Biochemistry (Proc. Nat'l. Acad. Sci. USA)* (1977) 74/10:4288–4292.
Turchinsky, M.F. et al. *FEBS Letters* (1974) 38/3:304–307.
Gilbson, K. et al. *Nucleic Acids Research* (1987) 15/16:5455–6467.
Meyer, Rich B. et al. *J. Am. Chem. Soc.* (1989) 111/22:8517–8519.
Telser, Joshua et al. *J. Am. Chem. Soc.* (1989) 111/18:7226–7232.
*Chemical Abstracts* (1980) 92/21:p. 20.
Glass, Robert E. *Gene Function: E. coli and its heritable elements*, Univ. of Calif. Press (1982) pp. 268–312.
Moser, Heinz E. et al. *Research Articles* (1987) Oct. 30:645–650.
Hartley, John A. et al. *biochemistry* (1990) 29/12:2985–2991.
Vlassov, Valentin V. et al. "Sequence–specific chemical modification of double–stranded DNA with alkylating oligodeoxyribonucleotide derivatives" *Gene* (1988) 72:313–322.
Uhlmann, E. et al. *Chemical Rivews* (1990) 90/4:544–584.
Moneesh Chatterjee et al. *J. Am. Chem. Soc.*, (1990) 112:6397–6399.
Shaw, Jeng–Pyng et al. *J. Am. Chem. Soc.*, (1991) 113:7765–7766.
Korre, D.G. et al. *Chemical Reviews* "Oligonucleotide Linked to Reactive Groups", Ed. by J. Cohen, Chapter 8, CRC Press, Inc., (1989) pp. 173–196.
John, Rainer et al. *Chem. Ber.* (1990) 123:133–136.
Orson, Frank M. *Nucleic Acids Research*, (1991) 19/12:3435–3441.
Gamper et al. Nucl. Acids Res. 14: 9943, 1986.
Robins et al., *J. Can, J. Chem.*, 60:554 (1982).
Robins et al., *J. Org. Chem.*, 48:1854 (1983).
Dale et al., *Proc. Natl. Acad. Sci, USA*, 70:2238 (1973).
Dale et al., *Biochemistry*, 14:2447 (1975).
Ruth et al., *J. Org. Chem.*, 43:2870 (1978).
Bergstrom et al., *J. Am. Chem. Soc.*, 100:8106 (1978).
Bigge et al., *J. Am. Chem. Soc.*, 102:2033 (1980).
Kobayashi, *Chem. Pharm. Bull.*, 21:941 (1973).
B.R. Baker, "Design of Active–Site–Directed Irreversible Enzyme Inhibitors," John Wiley and Sons Inc., New York, (1967).
Summerton and Bartlett, *J. Mol. Biol.*, 122:145 (1978).
Webb and Matteucci, *Nucleic Acids Res.*, 14:7661 (1986).
Iverson and Dervan, *Proc. Natl. Acad. Sci. USA*, 85:4615 (1988).
Green et al., *Ann Rev. Biochem.*, 55:569 (1986).
Paterson et al., *Proc. Natl. Acad. Sci.*, 74:4370 (1977).
Hastie et al., *Proc. Natl. Acad. Sci.*, 75:1217 (1978).
Zamecnik and Stephenson, *Proc. Natl. Acad. Sci.*, 75:280 (1978).
Stephenson et al., *Proc. Natl. Acad. Sci. USA*, 75:285 (1978).
Zamecnik et al., *Proc. Natl. Acad. Sci. USA*, 83:4143 (1986).
Blake et al., *Biochemistry*, 24:6139 (1985).
Gamper et al., *Natl. Acids Res.*, 14:9943 (1986).
Le Doan et al., *Nucleic Acids Res.*, 15:7749 (1987).
Sonveaux, *Bioorganic Chemistry*, 14:274 (1986).
Jones, in "Oligonucleotide Synthesis, a Practical Approach", M. J. Gait, Ed., IRL Press, pp. 23–34 (1984).
Langer et al., *Proc. Natl. Acad. Sci. USA*, 78:6633 (1981).
Arrand, "Preparation of Nucleic Acid Probes" in *Nucleic Acid Hybridisation, A Practical Approach*, Hames and Higgins, Eds., IRL Press, pp. 17–45 (1985).
Pardue, "In Situ Hybridisation" in *Nucleic Acid Hybridisation, A Practical Approach*, Hames and Higgins, Eds. IRL Press, pp. 179–202 (1985).
Gall and Pardue, *Proc. Natl. Acad. Sci., USA*, 63:378 (1969).
John et al., *Nature*, 223:582 (1969).
"Physical Biochemistry", Freifelder, D., W.H. Freeman & Co., pp. 537–542 (1982).
Tijssen, P., "Practice and Theory of Enzyme Immunoassays, Laboratory Techniques" in *Biochemistry and Molecular Biology*, Burdon, R.H. van Knippenberg, P.H. Eds., Elsevier, pp. 9–20 (1985).
Sinha et al., *Nucleic Acids Res.*, 12:4539 (1984).
Maxam et al., *Proc. Natl. Acad. Sci. USA*, 74:560 (1977).
Busso, Mariano; et al: "Nucleotide Dimers Suppress HIV Expression In Vitro" in: *Aids Research and Human Retroviruses*, vol. 4, No. 6, 1988.
Seela et al. (I), Helv. Chim, Acta, 71, 1813–1823 (1988).
Seela et al. (II), Helv. Chim, Acta, 71, 1191–1198 (1988).
Seela et al. (III), Nucleic Acids Research, 14, 1825–1844 (1986).
Hecht et al. Biochemistry, 15, 1005–1015 (1976).
Fieser et al., Reagents for Organic Synthesis, John Wiley and Sons, New York, New York, 1967, vol. 1, p. 837.
Kochetkov et al., Organic Chemistry of Nucleic Acids, Part B, Plenum Press, New York, New York, 1972, p. 375.
Sinha et al. *Nucleic Acids Research*, 16(6), 2659–2669 (1988).

CROSS-LINKING OLIGONUCLEOTIDES

CROSS REFERENCE TO RELATED APPLICATIONS

This application is a continuation of application Ser. No. 08/049,807, filed Apr. 20, 1993, now abandoned which is in turn a continuation of application Ser. No. 07/353,857, filed May 18, 1989, now abandoned, which in turn is a continuation-in-part of application Ser. No. 250,474, filed on Sep. 28, 1988.

BACKGROUND OF THE INVENTION

This invention relates to nucleoside crosslinking agents and to the use of these compounds in the preparation of oligonucleotides. It also relates to derivatives of pyrazolo [3,4-d]pyrimidine which are useful as nucleic acid bases for the preparation of oligonucleotides.

Oligonucleotides are useful as diagnostic probes for the detection of "target" DNA or RNA sequences. In the past, such probes were made up of sequences of nucleic acid containing purine, pyrimidine or 7-deazapurine nucleotide bases (U.S. Pat. No. 4,711,955; Robins et al., *J. Can. J. Chem.*, 60:554 (1982); Robins et al., *J. Org. Chem.*, 48:1854 (1983)). The method for attaching chemical moieties to these bases has been via an acetoxy-mercuration reaction, which introduces covalently bound mercury atoms into the 5-position of the pyrimidine ring, the C-8 position of the purine ring or the C-7 position of a 7-deazapurine ring (Dale et al., *Proc. Natl. Acad. Sci. USA*, 70:2238 (1973); Dale et al., *Biochemistry*, 14:2447 (1975)), or by the reaction of organomercurial compounds with olefinic compounds in the presence of palladium catalysts (Ruth et al., *J. Org. Chem.*, 43:2870 (1978); Bergstrom et al., *J. Am. Chem. Soc.*, 100:8106 (1978); Bigge et al., *J. Am. Chem. Soc.*, 102:2033 (1980)).

The sugar component of oligonucleotide probes has been, until the present, composed of nucleic acid containing ribose or deoxyribose or, in one case, natural β-arabinose (patent publication EP 227,459).

A novel class of nucleotide base, the 3,4-disubstituted and 3,4,6-trisubstituted pyrazolo[3,4-d]-pyrimidines, has now been found which offers several advantages over the prior art. The de novo chemical synthesis of the pyrazolopyrimidine and the resulting nucleotide allows for the incorporation of a wide range of functional groups in a variety of different positions on the nucleotide base and for the use of different sugar moieties. Also, adenine, guanine and hypoxanthine analogs are obtained from a single nucleoside precursor. Additionally, the synthesis does not require the use of toxic heavy metals or expensive catalysts. Similar pyrazolo [3,4-d]pyrimidines are known (Kobayashi, *Chem. Pharm. Bull.*, 21:941 (1973)); however, the substituents on the group are different from those of the present invention and their only use is as xanthine oxidase inhibitors The concept of crosslinkable nucleotide probes for use in therapeutic and diagnostic applications is related to the pioneering work of B. R. Baker, "Design of Active-Site-Directed Irreversible Enzyme Inhibitors," Wiley, N.Y., (1967), who used what was termed "active-site-directed enzyme inhibitors" in chemotherapeutic applications.

In recent years, the concept of incorporating a crosslink in an oligonucleotide has been sporadically discussed in efforts to develop superior sequence probes. Knorre and Vlassov, *Prog. Nucl. Acid Res. Mol. Biol.*, 32:291 (1985), have discussed sequence-directed cross-linking ("complementary addressed modification") using an N-(2-chloroethyl)-N-methylaniline group attached to either the 3'- or 5¹-terminus of oligonucleotides. Summerton and Bartlett, *J. Mol. Biol.*, 122:145 (1978) have shown that an 8-atom chain, attached to a cytosine residue at its C-4 position and terminating in the highly reactive bromomethyl ketone group, can crosslink to the N-7 of guanosine.

Webb and Matteucci, *Nucleic Acids Res.*, 14:7661 (1986), have prepared oligonucleotides containing a 5-methyl-N,N-ethanocytosine base which is capable of slow crosslinking with a complementary strand. In a conceptually related alkylation via a linker arm within a DNA hybrid, Iverson and Dervan, *Proc. Natl. Acad. Sci. USA*, 85:4615 (1988), have shown opposite strand methylation, triggered by BrCN activation of a methylthio ether, predominately on a guanine base located two pairs from the base bearing the linker.

Oligonucleotides may be used as chemotherapeutic agents to control the expression of gene sequences unique to an invading organism, such as a virus, a fungus, a parasite or a bacterium. In nature, some RNA expression in bacteria is controlled by "antisense" RNA, which exerts its effect by forming RNA:RNA hybrids with complementary target RNAs and modulating or inactivating their biological activity. A variety of recent studies using plasmid vectors for the introduction of antisense RNAs into eukaryotic cells have shown that they effectively inhibit expression of mRNA targets in vivo (reviewed in Green, et al., *Ann. Rev. Biochem.* 55: 569–597 (1986)). Additionally, a specific mRNA amongst a large number of mRNAs can be selectively inactivated for protein synthesis by hybridization with a complementary DNA restriction fragment, which binds to the mRNA and prevents its translation into protein on ribosomes (Paterson, et al., *Proc. Natl. Acad. Sci* 74: 4370–4374 (1977); Hastie et al., *Proc. Natl. Acad. Sci.* 75: 1217–1221 (1978)).

In the first demonstration of the concept of using sequence-specific, antisense oligonucleotides as regulators of gene expression and as chemotherapeutic agents, Zamecnik and Stephenson, *Proc. Natl. Acad. Sci. USA*, 75:280 (1978), showed that a small antisense oligodeoxynucleotide probe can inhibit replication of Rous Sarcoma virus in cell culture, and that RSV viral RNA translation is inhibited under these conditions (Stephenson et al., *Proc. Natl. Acad. Sci. USA* 75:285 (1978)). Zamecnik et al., *Proc. Natl. Acad. Sci. USA*, 83:4143 (1986), have also shown that oligonucleotides complementary to portions of the HIV genome are capable of inhibiting protein expression and virus replication in cell culture. Inhibition of up to 95% was obtained with oligonucleotide concentrations of about 70 $\mu$M. Importantly, they showed with labeled phosphate studies that the oligonucleotides enter cells intact and are reasonably stable to metabolism.

Uncharged methylphosphonate oligodeoxynucleotides with a sequence complementary to the initiation codon regions of rabbit globin mRNA inhibited the translation of the mRNA in both cell-free systems and in rabbit reticulocytes (Blake et al., *Biochemistry* 24:6139 (1985)). Another uncharged methylphosphonate oligonucleotide analog, an 8-nucleotide sequence complementary to the acceptor splice junction of a mRNA of Herpes simplex virus, Type 1, can inhibit virus replication in intact Vero cells. However, fairly high concentrations (>25 mM) of this nonionic probe were required for this inhibition.

Although the impact of crosslinking oligonucleotides in the chemotherapeutic field might be of great significance, their impact in DNA probe-based diagnostics is of equally great importance. The ability to covalently crosslink probe-target hybrids has the potential to dramatically improve background and sensitivity limits in diagnostic assays as well as permit novel assay formats. Specific innovations (discussed previously by Gamper et al., *Nucl. Acids Res.*, 14, 9943 (1988)) include:

(a) incorporation of a denaturing wash step to remove background;

(b) use of the crosslink as an additional tier of discrimination;

(c) crosslinking occurring at or near the melting temperature of the expected hybrid to insure exquisite specificity and to substantially reduce secondary structure in the target, thereby increasing the efficiency of hybrid formation; and (d) novel solution hybridization formats as exemplified by the Reverse Southern protocol.

The concept of crosslinking, however, suggests potential problems that must be circumvented. For instance, the oligonucleotide containing a crosslinking arm might covalently bond to the target sequence so readily that mismatching of sequences will occur, possibly resulting in host toxicity. On the other hand, the crosslinking reaction must be fast enough to occur before correctly matched sequences can dissociate.

This issue can be addressed by constructing an oligonucleotide that, upon hybridization, results in a duplex whose $T_m$ is just above the physiological temperature of 37° C. Thus, even a single mismatched base will prevent hybrid formation and therefore crosslinkage. The optimization can be accomplished by judicious choice of oligonucleotide length and base composition, as well as position of the modified base within the probe. The probe must be long enough, however, to insure specific targeting of a unique site.

European Patent Application No. 86309090.8 describes the formation of chemically modified DNA probes such as 5-substituted uridinyl in which the substituent does not crosslink but contains a chemical or physical reporter group. WO8707611 describes a process for labeling DNA fragments such as by chemically modifying the fragment followed by reaction with a fluorescent dye. Yabusaki et al. in U.S. Pat. No. 4,599,303 disclose a scheme for covalently crosslinking oligonucleotides such as by formation of furocoumarin monoadducts of thymidine which are made to covalently bond to other nucleotides upon photoexcitation. EP 0259186 describes adducts of macromolecules and biotin which can be used as crosslinking nucleic acid hybridization probes. WO8503075 describes crosslinking disulfonic esters useful as nucleic acid fragmentation agents. DE3310337 describes the covalent crosslinking of single-stranded polynucleotides to such macromolecules as proteins with the resulting complex subsequently used as a marker in hybridization experiments in the search for complementary sequences in foreign polynucleotides.

A need exists for probe oligonucleotides, consisting of sufficient base sequences to identify target sequences with high specificity, that are provided with one or more crosslinking arms which readily form covalent bonds with specific complementary bases. Such oligonucleotides may be used as highly selective probes in hybridization assays. The oligonucleotides may also be used as antisensing agents of RNAs, e.g., in chemotherapy.

SUMMARY OF THE INVENTION

This invention is directed to crosslinking agents which accomplish crosslinking between specific sites on adjoining strands of oligonucleotides. The crosslinking reaction observed is of excellent specificity. The invention is also directed to oligonucleotides comprising at least one of these crosslinking agents and to the use of the resulting novel oligonucleotides for diagnostic and therapeutic purposes.

More particularly, the crosslinking agents of this invention are derivatives of nucleotide bases with a crosslinking arm and are of the following formula (I'):

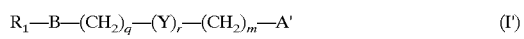

$$R_1-B-(CH_2)_q-(Y)_r-(CH_2)_m-A' \qquad (I')$$

wherein, $R_1$ is hydrogen, or a sugar moiety or analog thereof optionally substituted at its 3' or its 5' position with a phosphorus derivative attached to the sugar moiety by an oxygen and including groups $Q_1$ $Q_2$ and $Q_3$, or with a reactive precursor thereof suitable for nucleotide bond formation;

$Q_1$ is hydroxy, phosphate or diphosphate;

$Q_2$ is=O or =S;

$Q_3$ is $CH_2$—R', S—R', O—R', or N—R'R'';

each of R' and R'' is independently hydrogen or $c_{1-6}$ alkyl;

B is a nucleic acid base or analog thereof that is a component of an oligonucleotide;

Y is a functional linking group;

each of m and q is independently 0 to 8, inclusive;

r is 0 or 1; and

A' is a leaving group.

The invention also provides novel oligonucleotides comprising at least one of the above nucleotide base derivatives of formula I'.

Nucleotides of this invention and oligonucleotides into which the nucleotides have been incorporated may be used as probes. Since probe hybridization is reversible, albeit slow, it is desirable to ensure that each time a probe hybridizes with the correct target sequence, the probe is irreversibly attached to that sequence. The covalent crosslinking arm of the nucleotide bases of the present invention will permanently modify the target strand, or cause depurination. As such, the oligonucleotides of this invention are useful in the identification, isolation, localization and/or detection of complementary nucleic acid sequences of interest in cell-free and cellular systems. Therefore, the invention further provides a method for identifying target nucleic acid sequences, which method comprises utilizing an oligonucleotide probe comprising at least one of a labeled nucleotide base of the present invention.

This invention also provides novel substituted pyrazolo [3,4-d]pyrimidines which are useful as a nucleotide base in preparing nucleosides and nucleotides, rather than the natural purine or pyrimidine bases or the deazapurine analogs.

DETAILED DESCRIPTION OF THE INVENTION

Figure 1:
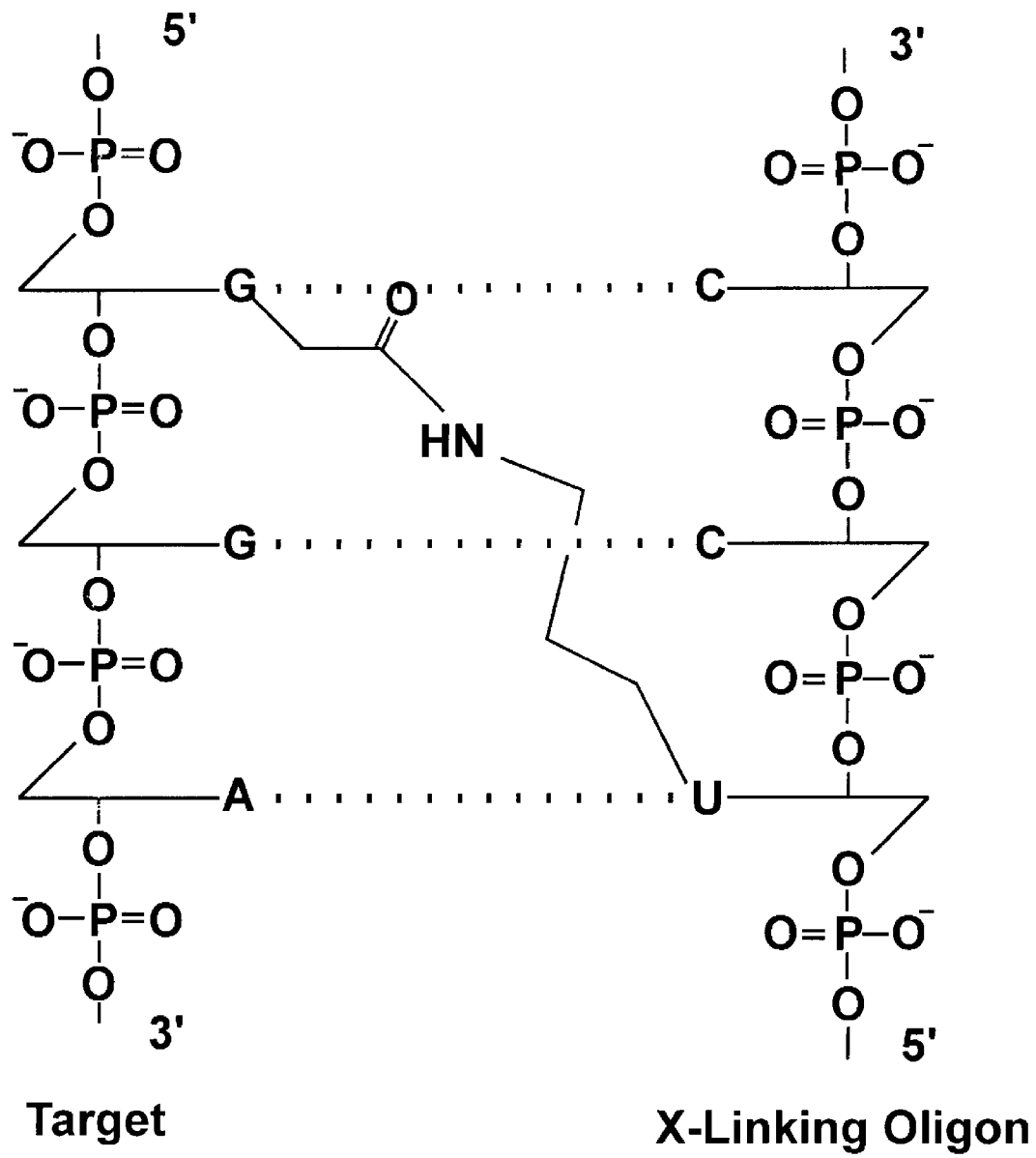
FIG. 1 depicts a modified deoxyuridine residue of an oligodeoxynucleotide crosslinked via an acetamidopropyl sidearm to a deoxyguanosine residue located two sites away from the complementary base along the 5' direction.

This invention provides novel substituted nucleotide bases with a crosslinking arm which are useful in preparing nucleosides and nucleotides and are useful as crosslinking agents. The substituted bases are of the following formula (I'):

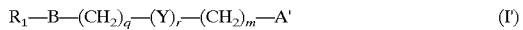

$$R_1-B-(CH_2)_q-(Y)_r-(CH_2)_m-A' \qquad (I')$$

wherein, $R_1$ is hydrogen, or a sugar moiety or analog thereof optionally substituted at its 3' or its 5' position with a phosphorus derivative attached to the sugar moiety by an oxygen and including groups $Q_1$, $Q_2$ and $Q_3$, or with a reactive precursor thereof suitable for nucleotide bond formation;

$Q_1$ is hydroxy, phosphate or diphosphate;

$Q_2$ is =O or =S;

$Q_3$ is $CH_2$—R', S—R', O—R', or N—R'R";

each of R' and R" is independently hydrogen or $C_{1-6}$alkyl;

B is a nucleic acid base or analog thereof that is a component of an oligonucleotide;

Y is a functional linking group;

each of m and q is independently 0 to 8, inclusive;

r is 0 or 1; and

A' is a leaving group.

In the practice of the present invention, the sugar moiety or analog thereof is selected from those useful as a component of a nucleotide. Such a moiety may be selected from, for example, ribose, deoxyribose, pentose, deoxypentose, hexose, deoxyhexose, glucose, arabinose, pentofuranose, xylose, lyxose, and cyclopentyl. The sugar moiety is preferably ribose, deoxyribose, arabinose or 2'-O-methylribose and embraces either anomer, α or β.

The phosphorus derivative attached to the sugar moiety is conveniently selected from, for example, monophosphate, diphosphate, triphosphate, alkyl phosphate, alkanephosphonate, phosphorothioate, phosphorodithioate, and the like.

A reactive precursor suitable for internucleotide bond formation is one which is useful during chain extension in the synthesis of an oligonucleotide. Reactive groups particularly useful in the present invention are those containing phosphorus. Phosphorus-containing groups suitable for internucleotide bond formation are preferably alkyl phosphorchloridites, alkyl phosphites or alkylphosphoramidites. Alternatively, activated phosphate diesters may be employed for this purpose.

The nucleic acid base or analog thereof (B) may be chosen from the purines, the pyrimidines, the deazapurines and the pyrazolopyrimidines. It is preferably selected from uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrrolo[2,3-d]pyrimidin-5-yl, 4-aminopyrazolo[3,4-d]pyrimidin-3-yl or 4-amino-6-oxopyrazolo[3,4-d]pyrimidin-3-yl, where the purines are attached to the sugar moiety of the oligonucleotides via the 9-position, the pyrimidines via the 1-position, the pyrrolopyrimidines via the 7-position and the pyrazolopyrimidines via the 1-position.

The functional linking group Y may be chosen from nucleophilic groups such as oxy, thio, amino or chemically blocked derivatives thereof, for example trifluoroacetamido, phthalimido, CONR', NR'CO, and $SO_2NR'$, where R'=H or $C_{1-6}$alkyl. Such functionalities, including aliphatic or aromatic amines, exhibit nucleophilic properties and are capable of serving as a point of attachment of the —$(CH_2)$m—A' group. Amino groups and blocked derivatives thereof are preferred.

The leaving group A' may be chosen from, for example, such groups as chloro, bromo, iodo, $SO_2R'''$, or $S^+R'''R''''$, where each of R''' and R'''' is independently $c_{1-6}$alkyl or aryl or R''' and R'''' together form a $C_{1-6}$alkylene bridge. Chloro, bromo and iodo are preferred. The leaving group will be altered by its leaving ability. Depending on the nature and reactivity of the particular leaving group, the group to be used is chosen in each case to give the desired specificity of the irreversibly binding probes.

Examination of double-stranded DNA by ball-and-stick models and high resolution computer graphics indicates that the 7-position of the purines and the 5-position of the pyrimidines lie in the major groove of the B-form duplex of double-stranded nucleic acids. These positions can be substituted with side chains of considerable bulk without interfering with the hybridization properties of the bases. These side arms may be introduced either by derivatization of dThd or dcyd, or by straightforward total synthesis of the heterocyclic base, followed by glycosylation. These modified nucleosides may be converted into the appropriate activated nucleotides for incorporation into oligonucleotides with an automated DNA synthesizer. With the pyrazolo[3,4-d]pyrimidines, which are analogs of adenine, the crosslinking arm is attached at the 3-position, which is equivalent to the 7-position of purine.

The crosslinking side chain should be of sufficient length to reach across the major groove from a purine 7- or 8-position, pyrimidine 5-position, pyrrolopyrimidine 5-position or pyrazolopyrimidine 3-position and reacting with the N-7 of a purine (preferably guanine) located above (on the oligomer 3'-side) the base pair containing the modified analog. Thus, the side chain should be of at least three atoms, preferably of at least five atoms and more preferably of at least six atoms in length. A generally preferred length of the side chain is from about 5 to about 9 carbon atoms.

To optimize strand crosslinking, it would be desirable to have the target strand base which is being attacked paired to the first or second base which is on the 3' side of the modified base in the oligonucleotide containing the crosslinking arm. For example, in the case where the target strand base under attack is a guanine, the target sequence for a probe containing a modified uracil should contain the complement GZA (preferably GGA), where Z is any base, with the probe oligonucleotide containing UZC (preferably UCC), where U is dUrd 5-substituted with the crosslinking arm. In oligonucleotides containing crosslinking adenine derivatives, for example, the adenine-modified $\underline{A}Z^1C$ triplet would target $GZ^1T$, where $Z^1$ is any base.

It has been found that when the modified base containing the crosslinking arm is a uracil and the target sequence is GGA, alkylation of the second guanine on the target's 5' side of the crosslinker-modified base pair is the exclusive action observed (as shown in FIG. 1). The crosslinking reaction seems to be very specific for the "best fit" of electrophile to nucleophile, i.e., two or more guanine residues may need to neighbor the complement of the modified base to discover the site of alkylation.

Two classes of modified 2'-deoxynucleosides have demonstrated particular usefulness in the present invention for incorporation into oligonucleotides as sequence-directed crosslinking agents. The first class is the 5-substituted-2'-deoxyuridines whose general structure is presented below:

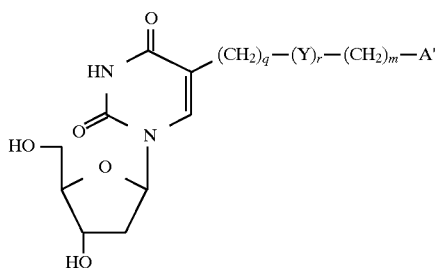

The 5-(substituted)-2'-deoxyuridines may be prepared by the routes shown in Schemes 1 and 2.

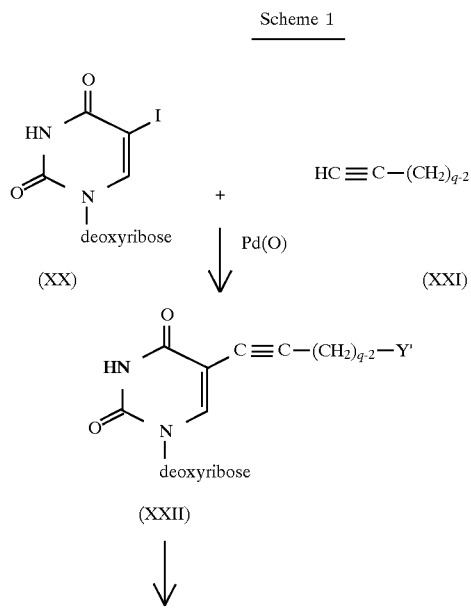

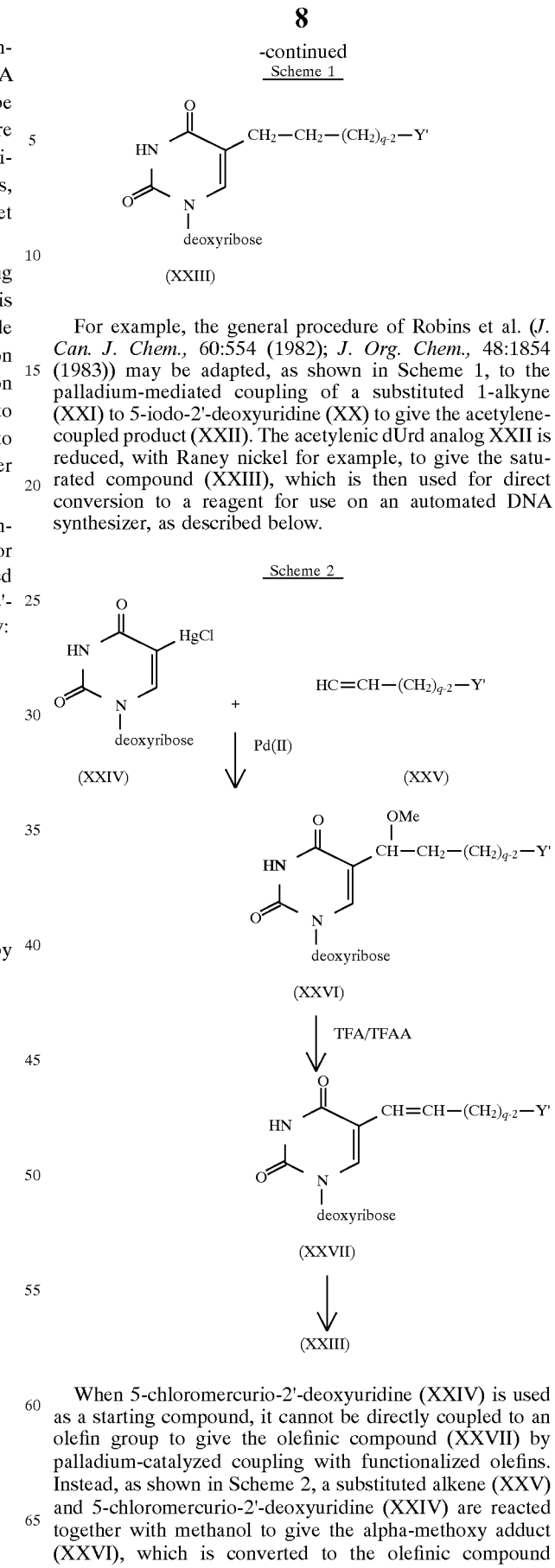

For example, the general procedure of Robins et al. (*J. Can. J. Chem.*, 60:554 (1982); *J. Org. Chem.*, 48:1854 (1983)) may be adapted, as shown in Scheme 1, to the palladium-mediated coupling of a substituted 1-alkyne (XXI) to 5-iodo-2'-deoxyuridine (XX) to give the acetylene-coupled product (XXII). The acetylenic dUrd analog XXII is reduced, with Raney nickel for example, to give the saturated compound (XXIII), which is then used for direct conversion to a reagent for use on an automated DNA synthesizer, as described below.

When 5-chloromercurio-2'-deoxyuridine (XXIV) is used as a starting compound, it cannot be directly coupled to an olefin group to give the olefinic compound (XXVII) by palladium-catalyzed coupling with functionalized olefins. Instead, as shown in Scheme 2, a substituted alkene (XXV) and 5-chloromercurio-2'-deoxyuridine (XXIV) are reacted together with methanol to give the alpha-methoxy adduct (XXVI), which is converted to the olefinic compound XXVII by trifluoroacetic acid and trifluoroacetic anhydride. Reduction gives the saturated compound (XXIII), to be converted to the DNA synthesizer-ready reagent as described below.

The second class of modified nucleoside is a group of 2'-deoxy-4-aminopyrazolo[3,4-d]pyrimidine derivatives. The general structure of these derivatives is presented below:

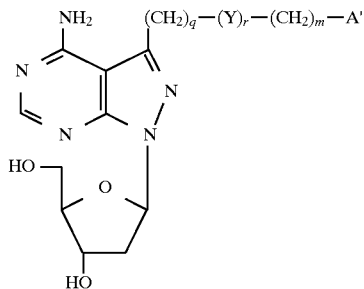

The above compounds are derived from a novel group of derivatives of 3,4-disubstituted and 3,4,6-trisubstituted pyrazolo[3,4-d]pyrimidines. The 3,4-di-substituted and 3,4,6-trisubstituted pyrazolo[3,4-d]pyrimidines and their synthesis are disclosed in commonly owned, copending application Ser. No. 250,474, the entire disclosure of which is incorporated herein by reference. They have the following formula (I):

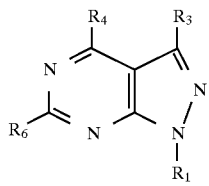

wherein, $R_1$ is hydrogen, or a sugar moiety or analog with a phosphorus derivative attached to the sugar moiety by an oxygen and including groups $Q_1$ $Q_2$ and $Q_3$, or with a reactive precursor thereof suitable for nucleotide bond formation; provided that when $R_3$ is hydrogen, then R cannot be hydrogen;

$Q_1$ is hydroxy, phosphate or diphosphate;

$Q_2$ is =O or =S;

$Q_3$ is $CH_2$—R', S—R', O—R', or N—R'R";

each of R' and R" is independently hydrogen or $C_{1-6}$alkyl;

$R_3$ is hydrogen or the group —W—$(X)_n$—A;

each of W and X is independently a chemical linker arm;

A is an intercalator, a metal ion chelator, an electrophilic crosslinker, a photoactivatable crosslinker, or a reporter group;

each of $R_4$ and $R_6$ is independently H, OR, SR, NHOR, $NH_2$, or $NH(CH_2)_tNH_2$;

R is H or $C_{1-6}$alkyl;

n is zero or one; and t is zero to twelve.

The synthesis of 3,4-disubstituted and 3,4,6-trisubstituted pyrazolo[3,4-d]pyrimidine nucleosides and their use as reagents for incorporation into nucleic acids either enzymatically or via chemical synthesis offers several advantages over current procedures. The de novo chemical synthesis of the nucleotide allows for the incorporation of a wide range of functional groups (e.g., $NH_2$, SH, OH, halogen, COOH, CN, $CONH_2$) and the use of different sugar moieties. Also, adenine, guanine, and hypoxanthine analogs are obtained from a single nucleoside precursor. And, the synthesis does not require the use of toxic heavy metals or expensive catalysts.

In the practice of the present invention, the sugar moiety or its analog is selected from those useful as a component of a nucleotide. Such a moiety may be selected from, for example, pentose, deoxypentose, hexose, deoxyhexose, ribose, deoxyribose, glucose, arabinose, pentofuranose, xylose, lyxose, and cyclopentyl. The sugar moiety is preferably ribose, deoxyribose, arabinose or 2'-O-methylribose and embraces either anomer, α or β.

The phosphorus derivative attached to the sugar moiety is conveniently selected from, for example, monophosphate, diphosphate, triphosphate, alkyl phosphate, alkanephosphonate, phosphorothioate, phosphorodithioate, and the like.

A reactive precursor suitable for internucleotide bond formation is one which is useful during chain extension in the synthesis of an oligonucleotide. Reactive groups particularly useful in the present invention are those containing phosphorus. Phosphorus-containing groups suitable for internucleotide bond formation are preferably alkyl phosphorchloridites, alkyl phosphites or alkylphosphoramidites. Alternatively, activated phosphate diesters may be employed for this purpose.

In the above formula I, a chemical linker arm (W alone or together with X) serves to make the functional group (A) more able to readily interact with antibodies, detector proteins, or chemical reagents, for example. The linkage holds the functional group away from the base when the base is paired with another within the double-stranded complex. Linker arms may include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or such groups substituted at a terminal point with nucleophilic groups such as oxy, thio, amino or chemically blocked derivatives thereof (e.g., trifluoroacetamido, phthalimido, CONR', NR'CO, and $SO_2NR'$, where R'=H or $C_{1-6}$alkyl). Such functionalities, including aliphatic or aromatic amines, exhibit nucleophilic properties and are capable of serving as a point of attachment of the functional group (A).

The linker arm moiety (W alone or together with X) is preferably of at least three atoms and more preferably of at least five atoms. The terminal nucleophilic group is preferably amino or chemically blocked derivatives thereof.

Intercalators are planar aromatic bi-, tri- or polycyclic molecules which can insert themselves between two adjacent base pairs in a double-stranded helix of nucleic acid. Intercalators have been used to cause frameshift mutations in DNA and RNA. It has also recently been shown that when an intercalator is covalently bound via a linker arm ("tethered") to the end of a deoxyoligonucleotide, it increases the binding affinity of the oligonucleotide for its target sequence, resulting in strongly enhanced stability of the complementary sequence complex. At least some of the tethered intercalators also protect the oligonucleotide against exonucleases, but not against endonucleases. See, Sun et al., *Nucleic Acids Res.*, 15:6149–6158 (1987); Le Doan et al., *Nucleic Acids Res.*, 15:7749–7760 (1987). Examples of tetherable intercalating agents are oxazolopyridocarbazole, acridine orange, proflavine, acriflavine and derivatives of proflavine and acridine such as 3-azido-6-(3-bromopropylamino)acridine, 3-amino-6-(3-bromopentylamino)-acridine, and 3-methoxy-6-chloro-9-(5-hydroxypentylamino)acridine.

Oligonucleotides capable of crosslinking to the complementary sequence of target nucleic acids are valuable in chemotherapy because they increase the efficiency of inhibition of MRNA translation or gene expression control by covalent attachment of the oligonucleotide to the target sequence. This can be accomplished by crosslinking agents being covalently attached to the oligonucleotide, which can then be chemically activated to form crosslinkages which can then induce chain breaks in the target complementary sequence, thus inducing irreversible damage in the sequence. Examples of electrophilic crosslinking moieties include alpha-halocarbonyl compounds, 2-chloroethylamines and epoxides.

When oligonucleotides comprising at least one nucleotide base moiety of the invention are utilized as a probe in nucleic acid assays, a label is attached to detect the presence of hybrid polynucleotides. Such labels act as reporter groups and act as means for detecting duplex formation between the target nucleotides and their complementary oligonucleotide probes.

A reporter group as used herein is a group which has a physical or chemical characteristic which can be measured or detected. Detectability may be provided by such characteristics as color change, luminescence, fluorescence, or radioactivity; or it may be provided by the ability of the reporter group to serve as a ligand recognition site.

The pyrazolopyrimidines of the present invention of formula I where $R_1$ is hydrogen may be prepared by the procedures outlined below and as set forth by Kobayashi in *Chem. Pharm. Bull.*, 21:941–951 (1973), the disclosure of which is incorporated herein by reference.

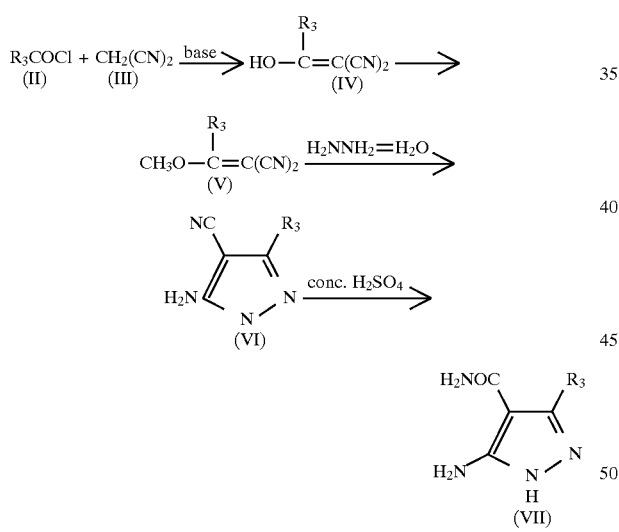

In general, malononitrile (III) is treated with acyl halide (II) in the presence of a base to yield acylmalononitrile (IV), which is subsequently methylated with dimethyl sulfate or diazomethane, for example, to give the substituted methoxymethylenemalononitrile (V). This compound is then reacted with hydrazine hydrate in boiling alcohol to give the 3-substituted-5-aminopyrazole-4-carbonitrile (VI), which is treated with cold concentrated sulfuric acid to give the 3-substituted-5-aminopyrazole-4-carboxamide (VII).

The carboxamide (VII) may alternatively be prepared by treating cyanoacetamide (XII) with acid halide (II) to give the acylcyanoacetamide (XIII), which is then methylated, and the resulting methoxy compound (XIV) is reacted with hydrazine hydrate.

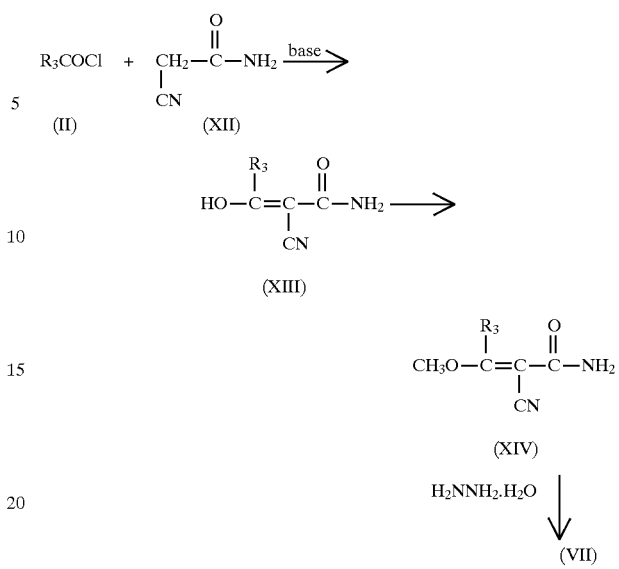

Syntheses of pyrazolo[3,4-d]pyrimidines are accomplished from the two pyrazole intermediates, VI and VII. Thus, 3,4-disubstituted pyrazolo[3,4-d]pyrimidines (VIII and X) are obtained by treating the corresponding VI and VII with boiling formamide. Alternatively, VI may be treated with dialkoxymethyl ester of a carboxylic acid, at room temperature or above room temperature, and then with ammonia to give VIII, and VII may be treated with dialkoxymethyl ester of a carboxylic acid (without subsequent ammonia treatment), at room temperature or above room temperature, to give compound X. 3,4,6-Trisubstituted pyrazolo[3,4-d]pyrimidines (IX and XI) are obtained by fusing the corresponding VI and VII with urea and thiourea $(H_2N)_2C=R_6$ (where $R_6$ is O or S). Alternatively, VI and VII may be treated with an alkyl xanthate salt such as potassium ethyl xanthate and with alkyl halide such as methyl iodide, at a temperature above room temperature, followed by oxidation by a peroxide such as m-chloroperbenzoic acid (MCPBA) and subsequent treatment with ammonia to give IX and XI, respectively, where $R_6$ is $NH_2$.

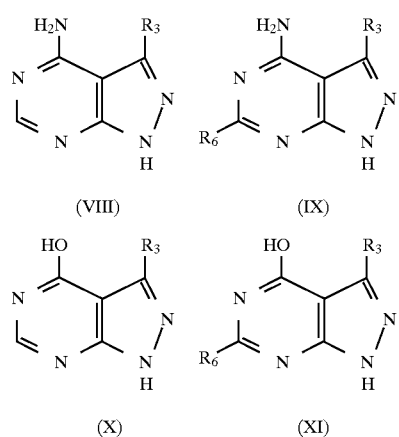

The compounds of formula I may be recovered from the reaction mixture in which they are formed by established procedures.

In the compounds of formula I where $R_1$ is a sugar moiety, the sugar may be either added to the 1-position of the pyrazole VI or VII prior to further treatment or added to the 1-position of the pyrazolo[3,4-d]pyrimidine VIII, IX, X or XI. To add the sugar, the pyrazole or pyrazolopyrimidine is treated with sodium hydride and then with the glycosyl halide of the blocked sugar.

Oligonucleotides of the present invention may comprise at least one and up to all of their nucleotides from the substituted pyrazolo[3,4-d]pyrimidines of formula I and/or at least one and up to all of their nucleotides from the substituted nucleotide bases of formula I'.

To prepare oligonucleotides, protective groups are introduced onto the nucleosides of formula I or formula I' and the nucleosides are activated for use in the synthesis of oligonucleotides. The conversion to protected, activated forms follows the procedures as described for 2'-deoxynucleosides in detail in several reviews. See, Sonveaux, *Bioorganic Chemistry*, 14: 274–325 (1986); Jones, in "Oligonucleotide Synthesis, a Practical Approach", M. J. Gait, Ed., IRL Press, p. 23–34 (1984).

The activated nucleotides are incorporated into oligonucleotides in a manner analogous to that for DNA and RNA nucleotides, in that the correct nucleotides will be sequentially linked to form a chain of nucleotides which is complementary to a sequence of nucleotides in target DNA or RNA. The nucleotides may be incorporated either enzymatically or via chemical synthesis. The nucleotides may be converted to their 5'O-dimethoxytrityl-3'-(N,N-diisopropyl) phosphoramidite cyanoethyl ester derivatives, and incorporated into synthetic oligonucleotides following the procedures in "Oligonucleotide Synthesis: A Practical Approach", supra. The N-protecting groups are then removed, along with the other oligonucleotide blocking groups, by post-synthesis aminolysis, by procedures generally known in the art.

In a preferred embodiment, the activated nucleotides may be used directly on an automated DNA synthesizer according to the procedures and instructions of the particular synthesizer employed. The oligonucleotides may be prepared on the synthesizer using the standard commercial phosphoramidite or H-phosphonate chemistries.

In another preferred embodiment, the amino-pyrazolopyrimidine nucleotide triphosphates may substitute for an adenine using the nick translation procedure, as described by Langer et al., *Proc. Natl. Acad. Sci. USA*, 78:6633–6637 (1981), the disclosure of which is incorporated herein by reference.

The leaving group, such as a haloacyl group, may be added to the aminoalkyl tails (—CH$_2$)q—Y) following incorporation into oligonucleotides and removal of any blocking groups. For example, addition of an α-haloacetamide may be verified by a changed mobility of the modified compound on HPLC, corresponding to the removal of the positive charge of the amino group, and by subsequent readdition of a positive charge by reaction with 2-amino-ethanethiol to give a derivative with reverse phase HPLC mobility similar to the original aminoalkyl-oligonucleotide.

In specific embodiments, each of the following electrophilic leaving groups were attached to an aminopropyl group on human papillomavirus (HPV) probes: bromoacetyl, iodoacetyl and the less reactive but conformationally more flexible 4-bromobutyryl. Bromoacetyl and iodoacetyl were found to be of equal reactivity in crosslinking.

An oligonucleotide probe according to the invention includes at least one labeled substituted pyrazolo[3,4-d]pyrimidine nucleotide moiety of formula I and/or at least one labeled substituted nucleotide base of formula I'.

Probes may be labeled by any one of several methods typically used in the art. A common method of detection is the use of autoradiography with $^3$H, $^{125}$I, $^{35}$S, $^{14}$C, or 32P labeled probes or the like. Other reporter groups include ligands which bind to antibodies labeled with fluorophores, chemiluminescent agents, and enzymes. Alternatively, probes can be conjugated directly with labels such as fluorophores, chemiluminescent agents, enzymes and enzyme substrates. Alternatively, the same components may be indirectly bonded through a ligand-antiligand complex, such as antibodies reactive with a ligand conjugated with label. The choice of label depends on sensitivity required, ease of conjugation with the probe, stability requirements, and available instrumentation.

The choice of label dictates the manner in which the label is incorporated into the probe. Radioactive probes are typically made using commercially available nucleotides containing the desired radioactive isotope. The radioactive nucleotides can be incorporated into probes, for example, by using DNA synthesizers, by nick-translation, by tailing of radioactive bases to the 3' end of probes with terminal transferase, by copying M13 plasmids having specific inserts with the Klenow fragment of DNA polymerase in the presence of radioactive dNTP's, or by transcribing RNA from templates using RNA polymerase in the presence of radioactive rNTP's.

Non-radioactive probes can be labeled directly with a signal (e.g., fluorophore, chemiluminescent agent or enzyme) or labeled indirectly by conjugation with a ligand. For example, a ligand molecule is covalently bound to the probe. This ligand then binds to a receptor molecule which is either inherently detectable or covalently bound to a detectable signal, such as an enzyme or photoreactive compound. Ligands and antiligands may be varied widely. Where a ligand has a natural "antiligand", namely ligands such as biotin, thyroxine, and cortisol, it can be used in conjunction with its labeled, naturally occurring antiligand. Alternatively, any haptenic or antigenic compound can be used in combination with a suitably labeled antibody. A preferred labeling method utilizes biotin-labeled analogs of oligonucleotides, as disclosed in Langer et al., *Proc. Natl. Acad. Sci. USA*, 78:6633–6637 (1981), which is incorporated herein by reference.

Enzymes of interest as reporter groups will primarily be hydrolases, particularly phosphatases, esterases, ureases and glycosidases, or oxidoreductases, particularly peroxidases. Fluorescent compounds include fluorescein and its derivatives, rhodamine and its derivatives, dansyl, umbelliferone, rare earths, etc. Chemiluminescers include luciferin, acridinium esters and 2,3-dihydrophthalazinediones, e.g., luminol.

The specific hybridization conditions are not critical and will vary in accordance with the investigator's preferences and needs. Various hybridization solutions may be employed, comprising from about 20% to about 60% volume, preferably about 30%, of a polar organic solvent. A common hybridization solution employs about 30–60% v/v formamide, about 0.5 to 1M sodium chloride, about 0.05 to 0.1M buffers, such as sodium citrate, Tris HCl, PIPES or HEPES, about 0.05% to 0.5% detergent, such as sodium dodecylsulfate, and between 1–10 mM EDTA, 0.01% to 5% ficoll (about 300–500 kdal), 0.1% to 5% polyvinylpyrrolidone (about 250–500 kdal), and 0.01% to 10% bovine serum albumin. Also included in the typical hybridization solution will be unlabeled carrier nucleic acids from about 0.1 to 5 mg/ml, e.g., partially fragmented calf thymus or salmon sperm, DNA, and/or partially fragmented yeast RNA and optionally from about 0.5% to 2% wt./vol. glycine. Other additives may also be included, such as volume exclusion agents which include a variety of polar water-soluble or swellable agents, such as anionic polyacrylate or polymethylacrylate, and charged saccharidic polymers, such as dextran sulfate.

The particular hybridization technique is not essential to the invention. Hybridization techniques are generally described in "Nucleic Acid Hybridization, A Practical Approach", Hames and Higgins, Eds., IRL Press, 1985; Gall and Pardue, *Proc. Natl. Acad. Sci.. U.S.A.,* 63:378–383 (1969); and John et al., *Nature,* 223:582–587 (1969). As improvements are made in hybridization techniques, they can readily be applied.

The amount of labeled probe which is present in the hybridization solution may vary widely. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more stringent, there must be a greater degree of complementarity between the probe and the target for the formation of a stable duplex. The degree of stringency can be controlled by temperature, ionic strength, the inclusion of polar organic solvents, and the like. For example, temperatures employed will normally be in the range of about 20° to 80° C., usually 25° to 75° C. For probes of 15–50 nucleotides in 50% formamide, the optimal temperature range can vary from 22°–65° C. With routine experimentation, one can define conditions which permit satisfactory hybridization at room temperature. The stringency of hybridization is also conveniently varied by changing the ionic strength and polarity of the reactant solution through manipulation of the concentration of formamide within the range of about 20% to about 50%.

Treatment with ultrasound by immersion of the reaction vessel into commercially available sonication baths can oftentimes accelerate the hybridization rates.

After hybridization at a temperature and time period appropriate for the particular hybridization solution used, the glass, plastic, or filter support to which the probe-target hybrid is attached is introduced into a wash solution typically containing similar reagents (e.g., sodium chloride, buffers, organic solvents and detergent), as provided in the hybridization solution. These reagents may be at similar concentrations as the hybridization medium, but often they are at lower concentrations when more stringent washing conditions are desired. The time period for which the support is maintained in the wash solutions may vary from minutes to several hours or more.

Either the hybridization or the wash medium can be stringent. After appropriate stringent washing, the correct hybridization complex may now be detected in accordance with the nature of the label.

The probe may be conjugated directly with the label. For example, where the label is radioactive, the support surface with associated hybridization complex substrate is exposed to X-ray film. Where the label is fluorescent, the sample is detected by first irradiating it with light of a particular wavelength. The sample absorbs this light and then emits light of a different wavelength which is picked up by a detector ("Physical Biochemistry", Freifelder, D., W. H. Freeman & Co., 1982, pp. 537–542). Where the label is an enzyme, the sample is detected by incubation with an appropriate substrate for the enzyme. The signal generated may be a colored precipitate, a colored or fluorescent soluble material, or photons generated by bioluminescence or chemiluminescence. The preferred label for dipstick assays generates a colored precipitate to indicate a positive reading. For example, alkaline phosphatase will dephosphorylate indoxyl phosphate which then will participate in a reduction reaction to convert tetrazolium salts to highly colored and insoluble formazans.

Detection of a hybridization complex may require the binding of a signal generating complex to a duplex of target and probe polynucleotides or nucleic acids. Typically, such binding occurs through ligand and antiligand interactions as between a ligand-conjugated probe and an antiligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays, Laboratory Techniques in Biochemistry and Molecular Biology", Burdon, R. H., van Knippenberg, P. H., Eds., Elsevier, 1985, pp. 9–20).

The amount of labeled probe present in the hybridization solution may vary widely, depending upon the nature of the label, the amount of the labeled probe that can reasonably bind to the cellular target nucleic acid, and the precise stringency of the hybridization medium and/or wash medium. Generally, substantial probe excesses over the stoichiometric amount of the target will be employed to enhance the rate of binding of the probe to the target nucleic acids.

The invention is also directed to a method for identifying target nucleic acid sequences, which method comprises utilizing an oligonucleotide probe including at least one labeled substituted nucleotide moiety of formula I and/or formula I'.

In one embodiment, the method comprises the steps of:
(a) denaturing nucleic acids in the sample to be tested;
(b) hybridizing to the target nucleic acids an oligonucleotide probe including at least one labeled substituted nucleotide moiety of formula I or formula I', wherein the probe comprises a sequence complementary to that of the target nucleic acids;
(c) washing the sample to remove unbound probe;
(d) incubating the sample with detection agents; and
(e) inspecting the sample.

The above method may be conducted following procedures well known in the art.

An assay for identifying target nucleic acid sequences utilizing an oligonucleotide probe including at least one labeled substituted nucleotide moiety of formula I and/or formula I' and comprising the above method is contemplated for carrying out the invention. Such an assay may be provided in kit form. For example, a typical kit will include a probe reagent component comprising an oligonucleotide including at least one labeled nucleotide moiety of formula I or formula I', the oligonucleotide having a sequence complementary to that of the target nucleic acids; a denaturation reagent for converting double-stranded nucleic acid to single-stranded nucleic acid; and a hybridization reaction mixture. The kit can also include a signal-generating system, such as an enzyme for example, and a substrate for the system.

The following examples are provided to illustrate the present invention without limiting same. "RT" means room temperature.

General

Thin layer chromatography was performed on silica gel 60 F 254 plates (Analtech) using the following solvent mixtures: A- 90% methylene chloride:10% methanol; B- 50% ethyl acetate:50% hexanes; C- 70% ethyl acetate: 10% methanol:10% water:10% acetone; D- 50% ether:50% hexanes. Flash chromatography was performed using 60 F 254 silica (Merck). Oligonucleotides were synthesized on an Applied Biosystems Model 380B Synthesizer. Oligonucleotides were isotopically labeled using T4 Polynucleotide kinase (BRL) and $\tau$-$^{32}$P-ATP (New England Nuclear).

EXAMPLE 1

6-(Tritylamino)caproic Acid

6-Aminocaproic acid (26 g, 0.2 mole) was dissolved in dichloromethane (200 mL) by the addition of triethylamine (100 mL). Trityl chloride (120 g, 0.45 mole) was added and the solution stirred for 36 hr. The resulting solution was extracted with 1N HCl and the organic layer evaporated to dryness. The residue was suspended in 2-propanol/1N NaOH (300 mL/100 mL) and refluxed for 3 hr. The solution was evaporated to a thick syrup and added to dichloromethane (500 mL). Water was added and acidified. The phases were separated, and the organic layer dried over sodium sulfate and evaporated to dryness. The residue was suspended in hot 2-propanol, cooled, and filtered to give 43.5 g (58%) of 6-(trityl-amino)caproic acid, useful as an intermediate compound.

EXAMPLE 2

5-(Tritylamino) pentylhydroxymethylenemalononitrile

To a dichloromethane solution of 6-(tritylamino)-caproic acid (20.0 g, 53 mmole) and triethylamine (20 mL) in an ice bath was added dropwise over 30 min isobutylchloroformate (8.3 mL, 64 mmole). After the mixture was stirred for 2 hr in an ice bath, freshly distilled malononitrile (4.2 g, 64 mmole) was added all at once. The solution was stirred for 2 hr in an ice bath and for 2 hr at RT. The dichloromethane solution was washed with ice cold 2N HCl (300 mL) and the biphasic mixture was filtered to remove product that precipitated (13.2 g). The phases were separated and the organic layer dried and evaporated to a thick syrup. The syrup was covered with dichloromethane and on standing deposited fine crystals of product. The crystals were filtered and dried to give 6.3 g for a total yield of 19.5 g (87%) of the product, which is useful as an intermediate.

EXAMPLE 3

5-(Tritylamino) pentylmethoxymethylenemalononitrile

A suspension of the malononitrile of Example 2 (13 g, 31 mmole) in ether/dichloromethane (900 mL/100 mL), cooled in an ice bath, was treated with a freshly prepared ethereal solution of diazomethane (from 50 mmole of Diazald® (Aldrich Chemical Company)). The solution was stirred for 6 hr and then neutralized with acetic acid (10 mL). The solution was evaporated to dryness and the residue chromatographed on silica gel using dichloromethane/acetone (4/1) as the eluent. Fractions containing product were pooled and evaporated to a syrup. The syrup was triturated with dichloromethane to induce crystallization. The crystals were filtered and dried to give 8.3 g (61%) of chromatographically pure product, useful as an intermediate compound.

EXAMPLE 4

5-Amino-3-[(5-tritylamino)pentyl]pyrazole-4-carbonitrile

To a methanol solution (100 mL) of the product of Example 3 (7.0 g, 16 mmole) in an ice bath was added hydrazine monohydrate (7.8 mL, 160 mmole) dropwise over 15 min. After stirring for 30 min in an ice bath, the solution was evaporated to dryness. The residue was suspended in cold methanol and filtered to give 7.1 g (100%) of 5-amino-3-[(5-tritylamino)pentyl]pyrazole-4-carbonitrile, useful as an intermediate, after drying. An analytical sample was prepared by recrystallization from water.

EXAMPLE 5

5-Amino-1-(2-deoxy-3,5-di-$\underline{O}$-toluoyl-β-$\underline{D}$-erythropentofuranosyl)-3-[(5-tritylamino) pentyl]pyrazole-4-carbonitrile An ice cold solution of the carbonitrile from Example 4 (3.5 g, 8 mmole) was treated with sodium hydride and stirred for 30 min at 0°–4° C. 1-Chloro-1,2-dideoxy-3,5-di-O-toluoylribofuranose was added and the solution stirred for 1 hr at 0°–4° C. The solution was poured into a saturated solution of sodium bicarbonate and extracted with dichloromethane. The organic layer was dried over sodium sulfate and evaporated to dryness. The residue was flash chromatographed on silica gel using toluene/ethyl acetate (5/1) as eluent. Two major products were isolated and identified as the N-1 and N-2 isomers in 57% (3.6 g) and 20% (1.2 g) N-1 and N-2 yields, respectively. Approximately 1 g of a mixture of N-1 and N-2 isomers was also collected. Overall yield of glycosylated material was 5.8 g (92%). The N-1 isomer, 5-amino-1-(2-deoxy-3,5-di-O-toluoyl-β-$\underline{D}$-erythropentofuranosyl)-3-[(5-tritylamino)-pentyl] pyrazole-4-carbonitrile, was used without further purification in Example 6.

EXAMPLE 6

1-(2-Deoxy-β-$\underline{D}$-erythropentofuranosyl)-3-[5-(tritylamino)-pentyl] pyrazolo[3,4-d]pyrimidin-4-amine To a toluene (100 mL) solution of the pyrazole-4-carbonitrile of Example 5 (3.5 g, 4.4 mmole) was added diethoxymethyl acetate (1.1 mL, 6.7 mmole). The solution was kept at 80°–90° C. for 5 hr and then evaporated to a syrup. The syrup was dissolved in dichloromethane (10 mL) and added to ice cold methanolic ammonia (100 mL) in a glass pressure bottle. After two days at RT the contents of the bottle were evaporated to dryness. The residue was dissolved in methanol and adjusted to pH 8 with freshly prepared sodium methoxide to complete the deprotection. After stirring overnight the solution was treated with Dowex®-50 H+ resin, filtered, and evaporated to dryness. The residue was chromatographed on silica gel using acetone/hexane (3/2) as eluent to give 2.0 g (77%) of analytically pure product.

EXAMPLE 7

1-(2-Deoxy-β-$\underline{D}$-erythropentofuranosyl)-3-[5-(tritylamino)-pentyl] pyrazolo[3,4-$\underline{d}$]pyrimidin-4-amine 5'-monophosphate To an ice cold solution of the pyrazolopyrimidin-4-amine of Example 6 (250 mg, 0.43 mmole) in trimethyl phosphate (5 mL) was added phosphoryl chloride (50 μL) and the solution was kept at 0°–4° C. The reaction was monitored by reversed phase HPLC using a linear gradient from 0 to 100% acetonitrile in water over 25 min. After stirring for 5 hr, an additional aliquot of phosphoryl chloride (25 μL) was added and the solution was stirred another 30 min. The solution was poured into 0.1M ammonium bicarbonate and kept in the cold overnight. The solution was then extracted with ether and the aqueous layer evaporated to dryness. The residue was dissolved in water (5 mL) and purified by reversed phase HPLC using a 22mm ×50cm C18 column. The column was equilibrated in water and eluted with a gradient of 0 to 100% acetonitrile over 20 min. Fractions containing the desired material were pooled and lyophilized to give 160 mg (56%) of chromatographically pure nucleotide.

EXAMPLE 8

1-(2-Deoxy-β-D-erythropentofuranosyl) -3-(5-[ (6-biotinamido)-hexanamido]pentyl)pyrazolo[3,4-d]pyrimidin-4-amine 5'-monophosphate.

An ethanol solution (10 mL) of the nucleotide of Example 7, palladium hydroxide on carbon (50 mg), and cyclohexadiene (1 mL) was refluxed for 3 days, filtered, and evaporated to dryness. The residue was washed with dichloromethane, dissolved in DMF (1.5 mL) containing triethylamine (100 mL), and treated with N-hydroxysuccinimidyl biotinylaminocaproate (50 mg). After stirring overnight an additional amount of N-hydroxysuccinimidyl 6-biotinamidocaproate (50 mg) was added and the solution was stirred for 18 hr. The reaction mixture was evaporated to dryness and chromatographed following the procedure in Example 7. Fractions were pooled and lyophilized to give 80 mg of chromatographically pure biotinamido-substituted nucleotide.

EXAMPLE 9

1-(2-Deoxy-β-D-erythropentofuranosyl)-3-[5-(6-biotinamido)-hexanamidopentyl]pyrazolo[3,4-d]pyrimidin-4-amine 5'-triphosphate.

The monophosphate of Example 8 (80 mg, ca. 0.1 mmole) was dissolved in DMF with the addition of triethylamine (14 μL). Carbonyldiimidazole (81 mg, 0.5 mmole) was added and the solution stirred at RT for 18 hr. The solution was treated with methanol (40 μL), and after stirring for 30 min tributylammonium pyrophosphate (0.5 g in 0.5 mL DMF) was added. After stirring for 24 hr another aliquot of tributylammonium pyrophosphate was added and the solution was stirred overnight. The reaction mixture was evaporated to dryness and chromatographed following the procedure in Example 8. Two products were collected and were each separately treated with conc. ammonium hydroxide (1 mL) for 18 hr at 55° C. UV and HPLC analysis indicated that both products were identical after ammonia treatment and were pooled and lyophilized to give 35.2 mg of nucleoside triphosphate.

EXAMPLE 10

Nick-Translation Reaction

The triphosphate of Example 9 was incorporated into pHPV-16 using the nick tanslation protocol of Langer et al. (supra). The probe prepared with the triphosphate of Example 9 was compared with probe prepared using commercially available bio-11-dUTP (Sigma Chemical Co). No significant differences could be observed in both a filter hybridization and in in situ smears.

More specifically, the procedure involved the following materials and steps:

Materials:
DNase (ICN Biomedicals)-4 μg/mL
DNA polymerase 1 (U.S. Biochemicals)-8 U/mL
PHPV-16-2.16 mg/mL which is a plasmid containing the genomic sequence of human papillomavirus type 16.
10X-DP-1M Tris,pH7.5(20 mL); 0.5M DTT(80 mL); 1M MgCl$_2$(2.8 mL); H$_2$O (17 mL)
Nucleotides-Mix A-2 mM each dGTP, dCTP, TTP (Pharmacia)
Mix U-2 mM each dGTP, dCTP, dATP
Bio-11-dUTP-1.0 mg/mL (BRL)
Bio-12-dAPPTP-1.0 mg/mL
Steps:

To an ice cold mixture of 10X-DP (4 mL), pHPV-16 (2 mL), nucleotide mix A (6 mL), Bio-12-dAPPTP (2 mL), and H$_2$O (20 mL) was added DNase (1 mL) and DNA polymerase 1 (2.4 mL). The reaction mixture was incubated at 16° C. for 1 hr. The procedure was repeated using Bio-11-dUTP and nucleotide mix U in place of Bio-12-dAPPTP (comprising the triphosphate of Example 9) and nucleotide mix A.

Nucleic acid was isolated by ethanol precipitation and hybridized to pHPV-16 slotted onto nitrocellulose. The hybridized biotinylated probe was visualized by a streptavidin-alkaline phosphatase conjugate with BCIP/NBT substrate. Probe prepared using either biotinylated nucleotide gave identical signals. The probes were also tested in an in situ format on cervical smears and showed no qualitative differences in signal and background.

EXAMPLE 11

5-Amino-3-[(5-tritylamino)pentyl]pyrazole-4-carboxamide

Following the procedure of Example 2, except that cyanoacetamide is used instead of malononitrile, 5-(tritylamino)pentylhydroxymethylenecyanoacetamide is prepared from 6-(tritylamino)caproic acid. This is then treated with diazomethane to give the methoxy derivative, following the procedures of Example 3, which is then reacted with hydrazine monohydrate, as in Example 4, to give 5-amino-3- [(5-tritylamino)pentyl]pyrazole-4-carboxamide.

EXAMPLE 12

4-Hydroxy-6-methylthio-3-[(5-tritylamino)pentyl] pyrazolo-[3,4-d]pyrimidine.

The carboxamide from Example 11 is reacted with potassium ethyl xanthate and ethanol at an elevated temperature to give the potassium salt of 4-hydroxypyrazolo[3,4-d]pyrimidine-6-thiol. This salt is then reacted with iodomethane to give 4-hydroxy-6-methylthio-3-[(5-tritylamino)pentyl]pyrazolo[3,4-d]pyrimidine.

EXAMPLE 13

1-(2-Deoxy-β-D-erythropentofuranosyl)-4-hydroxy-3-[5-(tritylamino) pentyl]pyrazolo[3,4-d]pyrimidin-6-amine Following the procedure of Example 5, the pyrazolopyrimidine of Example 12 is treated with sodium hydride and reacted with 1-chloro-1,2-dideoxy-3,5-di-O-toluoylribofuranose. The resulting compound is reacted with MCPBA and with methanolic ammonia, and the toluoyl protecting groups are removed to give the product.

EXAMPLE 14

1-(2-Deoxy-β-D-erythropentofuranosyl)-4-hydroxy-3-[5-(6-biotin amido)hexanamidopentyl]pyrazolo[3,4-d]pyrimidin-6-amine 5'-monophosphate.

Following the procedure of Example 7, the pyrazolopyrimidine of Example 13 is reacted with phosphoryl chloride to give the corresponding 5'-monophosphate.

Following the procedure of Example 8, the above 5'-monophosphate is reacted with palladium/carbon and cyclohexadiene, and the residue is reacted with N-hydroxysuccinimidyl biotinylaminocaproate to give 1-(2-deoxy-β-D-erythropentofuranosyl)-4-hydroxy-3-[5-(6-biotinamido) hexanamidopentyl]pyrazolo[3,4-d]pyrimidin-6-amine 5'-monophosphate.

EXAMPLE 15

1-(2-Deoxy-β-D-erythropentofuranosyl)-4-hydroxy-3-[5-(6-biotin amido)hexanamidopentyl]pyrazolo[3,4-d]pyrimidin-6-amine 5'-triphosphate Following the procedure of Example 9, the 5'-monophosphate of Example 14 is treated with carbonyldiimidazole and then reacted with tributylammonium pyrophosphate to give the corresponding 5'-triphosphate.

EXAMPLE 16

1-(2-Deoxy-β-D-erythropentofuranosyl)-3-[5-(tritylamino)-pentyl]pyrazolo[3,4-d]pyrimidine-4-benzoylamine 1-(2-Deoxy-β-D-erythropentofuranosyl)-3-[5-(tritylamino)pentyl]pyrazolo[3,4-d]pyrimidine-4-amine from Example 6 is reacted with benzoyl chloride and pyridine to give 1-(2-deoxy-3,5-di-O-benzoyl-β-D-erythro-pentofuranosyl)-3-[5-(tritylamino)pentyl]pyrazolo[3,4-d]-pyrimidine-4-dibenzoylamine. This is treated with aqueous sodium hydroxide to partially deprotect the compound, giving 1-(2-deoxy-β-D-erythropentofuranosyl)-3-[5-(tritylamino)pentyl]pyrazolo[3,4-d]pyrimidine-4-benzoylamine.

EXAMPLE 17

1-(2-Deoxy-β-D-erythropentofuranosyl)-3-[5-(trifluoroacetamido) pentyl]pyrazolo[3,4-d]pyrimidine-4-benzoylamine Following the procedure of Example 8, the benzoylamine of Example 16 is treated with palladium hydroxide on carbon and then with trifluoroacetic anhydride to give 1-(2-deoxy-β-D-erythropentofuranosyl)-3-[5-(trifluoroacetamido)pentyl] pyrazolo[3,4-d]pyrimidine-4-benzoylamine.

EXAMPLE 18

1-(2-Deoxy-5-O-dimethoxytrityl-β-D-erythropentofuranosyl)-3-[5-(trifluoroacetamido) pentyl]pyrazolo[3,4-d]pyrimidine-4-benzoylamine 3'-O-(N,N-diisopropyl)phosphoramidite cyanoethyl ester The compound of Example 17 is reacted with dimethoxytrityl chloride and pyridine to give the corresponding 5'-dimethoxytrityl compound. This compound is then reacted with cyanoethyl chloro-N,N-diisopropyl- phosphoramidite (according to the method of Sinha et al., *Nucleic Acids Res.*, 12:4539 (1984)) to give the 3'-O-activated nucleoside.

EXAMPLE 19

5-(4-Phthalimidobut-1-yn-1-yl)-2'-deoxyuridine

5-Iodo-2'-deoxyuridine (354 mg, 1 mmol) was dissolved in 10 mL of dimethylformamide. Cuprous iodide (76 mg, 0.4 mmol), tetrakis(triphenylphosphine)palladium(0) (230 mg, 0.2 mmol), and triethylamine (200 mg, 2.0 mmol) were added. 4-Phthalimidobut-1-yne (300 mg, 1.5 mmol) was added all at once and the reaction kept at 60° C. for three hours. The clear yellow reaction was then evaporated and methylene chloride was added. Scratching of the flask induced crystallization of nearly all of the product which was filtered and recrystallized from 95% ethanol to give 335 mg (78%) of title compound as fine, feathery needles.

EXAMPLE 20

5-(4-Phthalimidobut-1-yl)-2'-deoxyuridine 1.00 Gram of deoxyridine from Example 19 was dissolved in 95% EtOH and about 3 g of neutral Raney nickel was added. After 48 hours, the catalyst was removed by cautious filtration and the filtrate was evaporated to a solid which was recrystallized from methanol-water to give 960 mg (97%) of the title compound.

EXAMPLE 21

5-(3-Iodoacetamidopropyl)-2'-deoxyuridine 5-(3-Trifluoroacetamidoprop-1-yl)-2'-deoxyuridine (0.3 mmol) is treated with ammonia and then with N-hydroxysuccinimidyl α-iodoacetate (0.5 mmol). The reaction mixture is evaporated to dryness and purified by chromatography to give 5-(3-iodoacetamidopropyl)-2'-deoxyuridine.

EXAMPLE 22

5-(4-(4-Bromobutyramido)butyl)-2'-deoxyuridine

Following the procedure of Example 21, 5-(4-phthalimidobut-1-yl)-2'-deoxyuridine, from Example 20, is treated with ammonia and then with N-hydroxysuccinimidyl 4-bromobutyrate to give 5-(4-(4-bromobutyramido)butyl)-2'-deoxyuridine.

Preparation of Synthetic Oligonucleotides

EXAMPLE 23

Phosphoramidite Preparation and DNA Synthesis

Nucleosides were 5'-dimethoxytritylated, following known procedures, to give around 85% yield, and the 3'-phosphoramidite was made using diisopropylamino β-cyanoethylchlorophosphite (as described in "Oligonucleotide Synthesis: A Practical Approach", supra) with diisopropyl-ethylamine in methylene chloride. The phosphoramidite was made into a 0.2N solution in acetonitrile and placed on the automated DNA synthesizer. Incorporation of these new and modified phosphoramidites gave incorporation similar to ordinary phosphoramidites (97–99% as judged by assay of the trityl color released by UV.)

Oligonucleotides were removed from the DNA synthesizer in tritylated form and deblocked using 30% ammonia at 55° C. for 6 hours. Ten µL of 0.5M sodium bicarbonate was added to prevent acidification during concentration. The oligonucleotide was evaporated to dryness under vacuum and redissolved in 1.0 mL water. The oligonucleotides were purified by HPLC using 15–55% acetonitrile in 0.1N triethylammonium acetate over 20 minutes. Unsubstituted oligonucleotides came off at 10 minutes; amino derivatives took 11–12 minutes. The desired oligonucleotide was collected and evaporated to dryness, then it was redissolved in 80% aqueous acetic acid for 90 minutes to remove the trityl group. Desalting was accomplished with a G25 Sephadex column and appropriate fractions were taken. The fractions were concentrated, brought to a specific volume, dilution reading taken to ascertain overall yield and an analytical HPLC done to assure purity. oligonucleotides were frozen at −20° C. until use.

Following the above procedures, the nucleoside 5-(3-trifluoroacetamidoprop-1-yl)-2'-deoxyuridine was converted to the 5'-O -dimethoxytrityl-3'-(N,N-diisopropyl) -phosphoramidite cyanoethyl ester derivative. This was added to a DNA synthesizer and the following 14-mer oligonucleotide sequence was prepared:

3'-CT TCC U$^1$TG TAG GTC-5' where U$^1$ is 5-(3-aminoprop-1-yl)-2 '-deoxyuridine (oligo A).

In the same manner, 5-(4-phthalimidobut-1-yl) -2'-deoxyuridine was converted to the 5'-O-dimethoxytrityl-3'-(N,N-diisopropyl)phosphoramidite cyanoethyl ester derivative and added to a DNA synthesizer to prepare the above 14-mer oligonucleotide sequence where U$^1$ is 5-(4-aminobut-1-yl)-2'-deoxyuridine (oligo C).

A corresponding 14-mer oligonucleotide was also prepared where U$^1$ is the unmodified deoxyuridine.

EXAMPLE 24

Derivatization of Oligonucleotides

In general, to add the crosslinking arm to an aminoalkyloligonucleotide, a solution of 10 µg of the aminoalkyloligonucleotide and a 100X molar excess of n-hydroxysuccinimide haloacylate such as α-haloacetate or 4-halobutyrate in 10 µL of 0.1M borate buffer, pH 8.5, was incubated at ambient temperature for 30 min. in the dark. The entire reaction was passed over a NAP-10 column equilibrated with and eluted with distilled water. Appropriate fractions based on UV absorbance were combined and the concentration was determined spectrophotometrically.

Introduction of the haloacyl moiety was examined by HPLC. A Zorbax® oligonucleotide column (Dupont) eluted with a 20 minute gradient of 60% to 80% B composed of: A (20% acetonitrile:80% 0.02 N NaH$_2$PO$_4$) and B (1.2 N NaCl in 20% acetonitrile:80% 0.02 N NaH$_2$PO$_4$). The presence of a reactive α-haloacyl moiety was indicated by return of the retention time of the α-haloacylamidoalkyl oligonucleotide to the corresponding aminoalkyl oligonucleotide after exposure to 1N cysteamine. Introduction of cysteamine created equivalent charge patterns between the aminoalkyl oligonucleotide and the a-haloacylamido oligonucleotide.

Following the above procedure, the 14-mer oligonucleotide:

3'-CT TCC U$^1$TG TAG GTC-5' where U$^1$ is 5-(3-aminoprop-1-yl)-2'-deoxyuridine (oligo A, Example 23), was reacted with n-hydroxysuccinimide α-iodoacetate to give the above 14-mer oligonucleotide where U$^1$ is 5-(3-iodoacetamidoprop-1-yl)-2'-deoxyuridine (oligo B).

Oligo A and oligo B, as well as the above 14-mer where U$^1$ is the unmodified deoxyuridine were resolved in the Zorbax column, all of identical sequence, with the following retention times: unmodified 14-mer, 9.31 min; aminopropyl 14-mer (oligo A), 7.36 min; and iodoacetamido-propyl 14-mer (oligo B), 10.09 min.

In the same manner, the aminopropyl 14-mer (oligo A) was reacted with N-hydroxysuccinimide 4-bromobutyrate to give the 14-mer where U$^1$ is 5-(3-(4-bromobutyramido) prop-1-yl)-2'-deoxyuridine.

Also, the aminobutyl 14-mer (oligo C, Example 23) was reacted with either N-hydroxysuccinimide α-iodoacetate or N-hydroxysuccinimide 4-bromobutyrate to give the 14-mer where U$^1$ is 5-(4-iodoacetamidobut-1-yl)-2'-deoxyuridine or 5-(4-(4-bromobutyramido)but-1-yl)-2'-deoxyuridine, respectively.

Assays

EXAMPLE 25

Assay of Crosslinking Reaction

The reaction of crosslinking a DNA probe to a target nucleic acid sequence contained 1 µg of haloacyl-amidoalkyl probe and 10 ng of $^{32}$P-labeled cordycepin-tailed target in 200 µL of 0.1M Tris, pH 8.0, and 0.9M NaCl incubated at 20° or 30° C. Aliquots were removed at 24- or 72-hour intervals and diluted in 20 µL of 10 mM cysteamine to quench the haloacylamido group. These solutions were stored at RT, and 1 µL was used for analysis by denaturing polyacrylamide gel electrophoresis (PAGE).

Following the above procedure, two model oligonucleotide sequences were utilized to evaluate the crosslinkage potential of the modified probe to its complement. The sequences, derived from human papilloma-virus (HPV) or human cytomegalovirus (CMV), are shown below:

HPV System:
```
              5       10      15      20      25      30
              :       :       :       :       :       :
Target: 5'-AGA CAG CAC AGA ATT CGA AGG AAC ATC CAG-3'
Probe:                              3'- CT TCC UTG TAG GCT-5'
```

CMV System:
```
              5       10      15      20
              :       :       :       :
Target: 5'-ACC GTC CTT GAC ACG ATG GAC TCC-3'
Probe:                       3'- GAA CTG TGC UAC CTC-5'
```

U = 5-[3-(α-iodoacetamido)- or 3-(4-bromobutyr-amido)-propyl]-2'-deoxyuridine, or
U = 5-[3-(α-iodoacetamido)- or 4-(4-bromobutyr-amido)-butyl]-2'-deoxyuridine.

The target for HPV is a 30-mer, and for CMV it is a 24-mer. The crosslinking probes were a 14-mer for HPV and two 15-mers for CMV. Each probe contained a single modified deoxyuridine designated as U in the sequences above.

Figure 2:
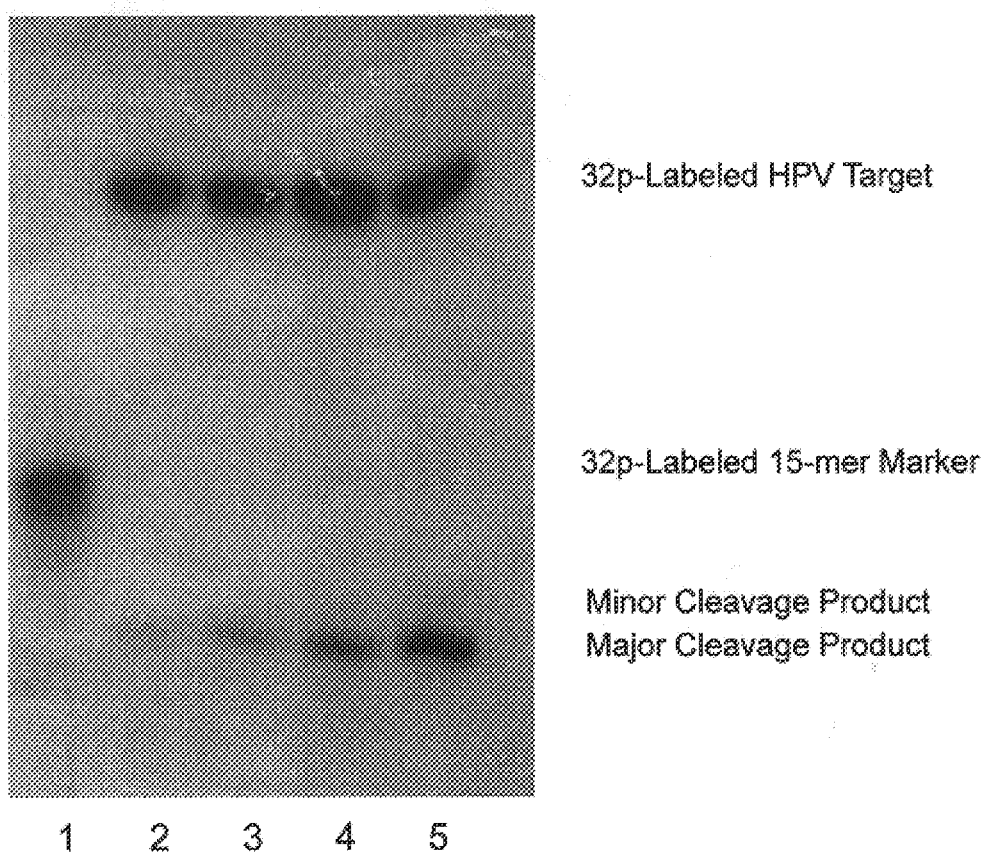
FIG. 2 depicts an autoradiogram of $^{32}P$ labeled HPV target and crosslinked product following cleavage at the 3' side of the crosslinked guanosine. Lane 1: 32P-labeled 15-mer size marker. Lane 2: 24 hour reaction at 20° C. Lane 3: 72 hour reaction at 20° C. Lane 4: 24 hour reaction at 30° C. Lane 5: 72 hour reaction at 30° C. Reactions were guenched with 2-aminoethanothiol and treated with piperidine sol on to effect cleavage.

Results of the reaction of HPV target with a limiting amount of crosslinking probe containing a 5-(3-iodoacetamidopropyl) sidearm are shown in FIG. 2. Analysis of the cleavage pattern on a denaturing PAGE gel showed the loss of the crosslinked hybrid with the concomitant appearance of a discrete low molecular weight band. The intensity of this band was dependent upon the extent of crosslinkage in the initial reaction. The localization of signal into two discrete bands on the gel strongly argues that no non-sequence-directed alkylation of either target or probe strands had occurred (including intramolecular probe alkylation).

Comparison to an authentic 15-mer run in an adjacent lane suggested that the major cleaved fragment is a 9-mer. Upon close examination of the original autoradiogram, a slower moving band of very weak intensity was visible. This pattern would be consistent with major alkylation at G-21 and minor alkylation at G-20. An examination of a Dreiding model of the crosslinkable HPV hybrid shows that the 5-(3-iodoacetamidopropyl) sidearm can contact the G-21 residue of the target strand with only minor distortion of the helix.

If alkylation occurs predominately at a guanosine on the target strand located two units on the 5' side of the modified-deoxyuridine base pair, the CMV sequence should not react. This result was in fact observed. The absence of reaction with CMV further supports the specificity of crosslinking scheme of the invention.

EXAMPLE 26

Time and Temperature Dependence

Time and temperature dependence studies were carried out with the HPV system of Example 25 where U is 5-(3-iodoacetamidoprop-1-yl)-2'-deoxyuridine. The target was $^{32}$P-labeled by cordycepin tailing with terminal transferase (Maniatis et al., "Molecular Cloning—A Laboratory Manual", Cold Spring Harbor Laboratory, 1982, p. 239) and incubated with excess probe in a pH 8.0 Tris buffer at either 20° or 30° C. Aliquots were removed after 0, 24, or 72 hours incubation, quenched with an equivalent volume of 10 mM mercaptoethylamine (which reacts with the iodoacetamide), and stored at RT for subsequent analysis by denaturing or non-denaturing PAGE.

Figure 3:
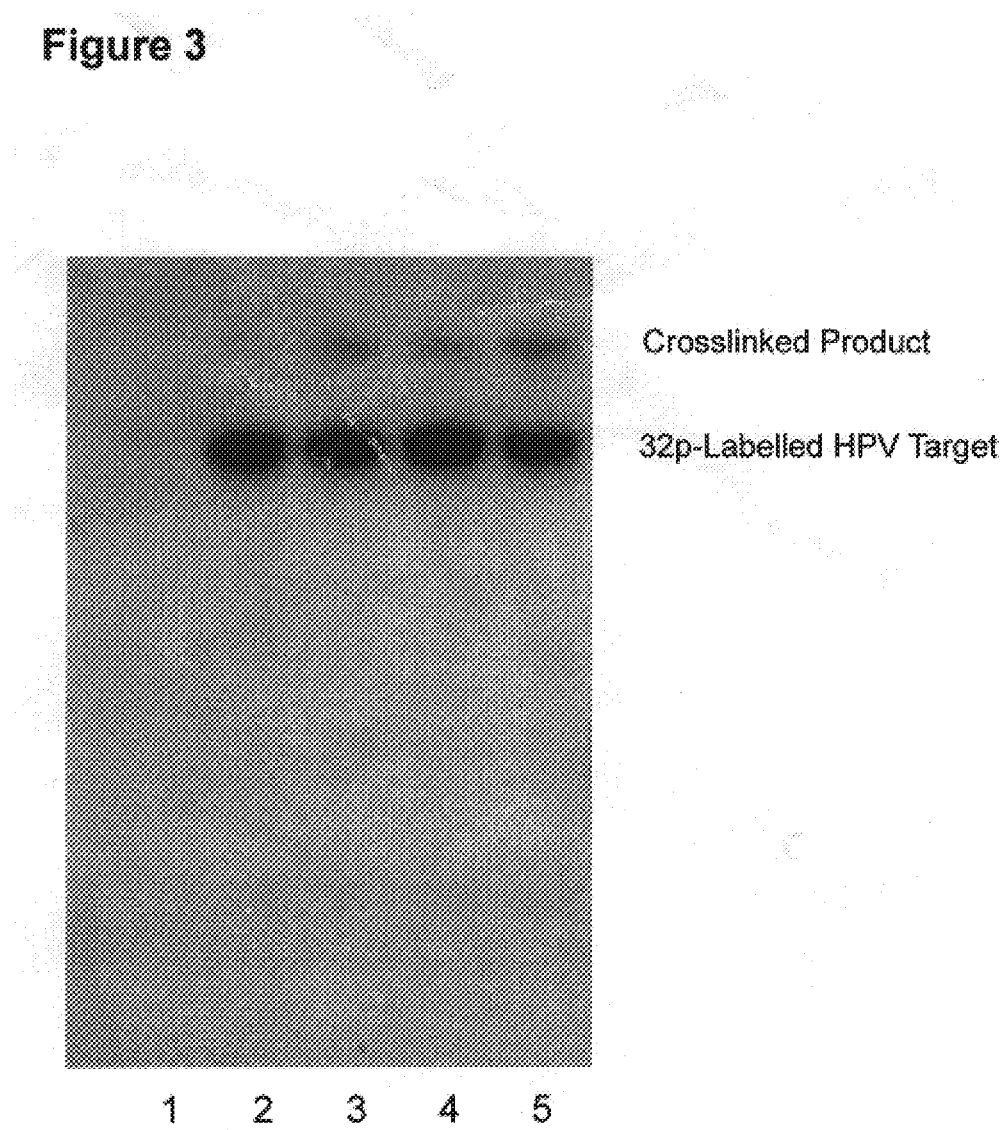
FIG. 3 depicts an autoradiogram of 32P labeled HPV target and crosslinked product showing hybrid separation by denaturing polyacrylamide gel electrophoresis. Lane 1: Control $^{32}$P-labeled CMV target. Lane 2: 24 hour reaction at 20° C. Lane 3: 72 hour reaction at 20° C. Lane 4: 24 hour reaction at 30° C. Lane 5: 72 hour reaction at 30° C. Reaction solutions were treated with 2-aminoethanothiol, which quenches the iodoacetamido group.

Crosslinkage of the hybrid, which was monitored by denaturing PAGE, was evident for the 24 and 72 hour time points at both temperatures (see FIG. 3). The amount of crosslinked hybrid increased with both temperature and time. Approximately 20% of the hybrid was crosslinked after 72 hours incubation at 30° C.

Separate experiments at a range of temperatures indicated that the half-life for crosslinking at 37° C. is approximately 2 days, and that the reaction is complete after 24 hours at 58° C. This time-dependent reaction implies that the iodoacetamido moiety does not hydrolyze or react with the buffer. The increased reaction rate at higher temperature indicates that the hybrid is maintained, and subsequently the rate of alkylation shows the expected increase with temperature.

EXAMPLE 27

Site Specificity of Alkylation

To elucidate the site specificity of alkylation, the crosslinked HPV hybrid of Example 25 (where U is 5-(3-iodoacetamidoprop-1-yl)-2'-deoxyuridine) was subjected to a 10% piperidine solution at 90° C. for 60 minutes. As shown by Maxam et al. (*Proc. Natl. Acad. Sci. USA,* 74: 560 (1977), this treatment quantitatively cleaves the target strand 3'-to the site of alkylation. The resulting data indicated that the alkylation of the second guanine above the crosslinker-modified base pair (i.e., the guanine above the target base) was the exclusive action observed, indicating that the crosslinking reaction in the HPV model system is remarkably specific.

---

What is claimed is:

1. An oligonucleotide having at least one nucleotide of the formula

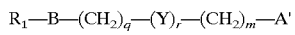

$R_1$—B—$(CH_2)_q$—$(Y)_r$—$(CH_2)_m$—A' wherein $R_1$ is a 1-($\beta$-D-ribofuranosyl) or 1-($\beta$-D-2-deoxyribofuranosyl) group which is optionally substituted on one or more of its hydroxyl functions with a Z group, wherein Z independently is methyl or a phosphate, thiophosphate, alkylphosphate or alkanephosphonate group;

B is a heterocyclic base selected from purine and pyrazolo[3,4-d]pyrimidine groups wherein the $(CH_2)_q$ group is attached to the 7-position or 8 position of the purine and 3-position of the pyrazolo[3,4-d]pyrimidine groups and the $R_1$ group is attached to the 9-position of the purine and to the 1-position of the pyrazolo[3,4-d]pyrimidine groups;

Y is a functional linking group selected from a group consisting of —O—, —S—, —NR'—, —NH—CO—, trifluoroacetamido and phtalimido groups where R' is H or $C_{1-6}$ alkyl, and at least one of the $(CH_2)_m$ and $(CH_2)_q$ groups is directly linked to the —O—, —S—, —NR'—, NH—CO—, trifluoroacetamido and phtalimido groups and the other of said $(CH_2)_m$ and $(CH_2)_q$ groups is linked to the heterocyclic base with a carbon to carbon bond;

m is 1 to 8, inclusive;

q is 0 to 8, inclusive;

r is 0 or 1; and

A' is a group selected from chloro, bromo, iodo, $SO_2R'''$, $S^+R'''R''''$ and a radical which activates the carbon to which it is attached for nucleophilic substitution, where each of R''' and R'''' is independently $C_{1-6}$ alkyl or aryl or R''' and R'''' together form a $C_{1-6}$ alkylene bridge.

2. An oligonucleotide according to claim 1 wherein B is selected from adenine-8-yl, guanine-8-yl, 4-aminopyrazolo[3,4-d]pyrimidin-3-yl, and 4-amino-6-oxopyrazolo[3,4-d]pyrimidin-3-yl groups.

3. An oligonucleotide according to claim 1 wherein m is 1, 2 or 3; q is 2, 3, or 4; and r is 1.

4. An oligonucleotide according to claim 1 wherein the $R_1$ group is 1-($\beta$-D-ribofuranosyl).

5. An oligonucleotide according to claim 1 wherein the $R_1$ group is 1-($\beta$-D-2-deoxyribofuranosyl).

6. An oligonucleotide according to claim 1 wherein the $R_1$ group is 1-($\beta$-D-2-O-methyl-ribofuranosyl).

7. An oligonucleotide according to claim 1 wherein the group —$(CH_2)_q$—$(Y)_r$—$(CH_2)_m$—A' is 3-iodoacetamidopropyl, 3-(4-bromobutyramido)propyl, 4-iodoacetamidobutyl, or 4-(4-bromobutyramido)butyl.

8. A compound of the formula

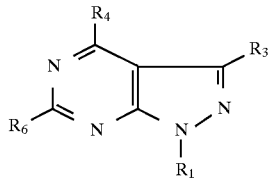

where $R_1$ is H, or a 1-(β-D-ribofuranosyl) or 1-(β-D-2-deoxyribofuranosyl) group which is optionally substituted on one or more of its hydroxyl functions with a Z group wherein Z independently is methyl or a phosphate, thiophosphate alkylphosphate or alkanephosphonate group, or a reactive precursor of said phosphate, thiophosphate, alkylphosphate or alkanephosphonate group which precursor is suitable for internucleotide bond formation;

$R_3$ is $(CH_2)_q$—$(Y)_r$—$(CH_2)_m$—A" where A" is a group selected from chloro, bromo, iodo, $SO_2R'''$, $S^+R'''R''''$ and a radical which activates the carbon to which it is attached for nucleophilic substitution, where each of $R'''$ and $R''''$ is independently $C_{1-6}$ alkyl or aryl or $R'''$ and $R''''$ together form a $C_{1-6}$ alkylene bridge, or A" is an intercalator group, a metal ion chelator or a reporter group;

Y is a functional linking group selected from a group consisting of —O—, —S—, —NR'—, —NH—CO—, trifluoroacetamido and phtalimido groups where R' is H or $C_{1-6}$ alkyl, and at least one of the $(CH_2)_m$ and $(CH_2)_q$ groups is directly linked to said —O—, —S—, —NR'—, NH—CO—, trifluoroacetamido and phtalimido groups and the other of said $(CH_2)_m$ and $(CH_2)_q$ groups is linked to the heterocyclic base with a carbon to carbon bond;

each of m and q is independently 0 to 8, inclusive; r is 0 or 1 provided that when A" is a group selected from chloro, bromo, iodo, $SO_2R'''$, $S^+R'''R''''$ and a radical which activates the carbon to which it is attached for nucleophilic substitution, then m is not 0;

each of $R_4$ and $R_6$ is independently H, OR, SR, NHOR, $NH_2$, or $NH(CH_2)_tNH_2$ where R is H or $C_{1-6}$alkyl and t is an integer from 0 to 12.

9. A compound in accordance with claim 8 where each of $R_4$ and $R_6$ is independently selected from a group consisting of H, OH and $NH_2$.

10. A compound of the formula

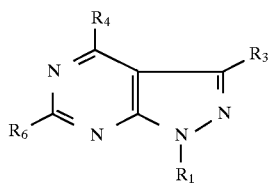

where $R_1$ is H, or a 1-(β-D-ribofuranosyl) or 1-(β-D-deoxyribofuranosyl) group which is optionally substituted on one or more of its hydroxyl functions with a Z group wherein Z independently is methyl or a phosphate, thiophosphate, alkylphosphate or alkanephosphonate group, or a reactive precursor of said phosphate, thiophosphate, alkylphosphate or alkanephosphonate group which precursor is suitable for internucleotide bond formation;

$R_3$ is $(CH_2)_q$—$(Y)_r$—$(CH_2)_m$—A" and A" is a reporter group;

Y is a functional linking group selected from a group consisting of —O—, —S—, —NR'—, —NH—CO—, trifluoroacetamido and phtalimido groups where R' is H or $C_{1-6}$ alkyl, and at least one of the $(CH_2)_m$ and $(CH_2)_q$ groups is directly linked to said —O—, —S—, —NR'—, NH—CO—, trifluoroacetamido and phtalimido groups and the other of said $(CH_2)_m$ and $(CH_2)_q$ groups is linked to the heterocyclic base with a carbon to carbon bond;

each of m and q is independently 0 to 8, inclusive; r is 0 or 1, and each of $R_4$ and R6 is independently H, OR, SR, NHOR, $NH_2$, or $NH(CH_2)_tNH_2$ where R is H or $C_{1-6}$alkyl and t is an integer from 0 to 12.

11. A compound in accordance with claim 10 where each of $R_4$ and $R_6$ is independently selected from a group consisting of H, OH and $NH_2$.

12. A compound in accordance with claim 11 where the reporter group is biotin or 2,4-dinitrobenzene.

13. An oligonucleotide having at least one nucleotide of the formula

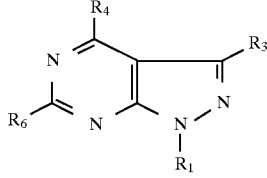

wherein $R_1$ is a 1-(β-D-ribofuranosyl) or 1-(β-D-2-deoxyribofuranosyl) group which is optionally substituted on one or more of its hydroxyl functions with a Z group wherein Z independently is methyl or a phosphate, thiophosphate, alkylphosphate or alkanephosphonate group;

$R_3$ is $(CH_2)_q$—$(Y)_r$—$(CH_2)_m$—A and A is a reporter group;

Y is a functional linking group selected from a group consisting of —O—, —S—, —NR'—, —NH—CO—, trifluoroacetamido and phtalimido groups where R' is H or $C_{1-6}$ alkyl, and at least one of the $(CH_2)_m$ and $(CH_2)_q$ groups is directly linked to said —O—, —S—, —NR'—, NH—CO—,trifluoroacetamido and phtalimido groups and the other of said $(CH_2)_m$ and $(CH_2)_q$ groups is linked to the heterocyclic base with a carbon to carbon bond;

each of m and q is independently 0 to 8, inclusive; r is 0 or 1, and each of $R_4$ and R6 is independently H, OR, SR, NHOR, $NH_2$, or $NH(CH_2)_tNH_2$ where R is H or $C_{1-6}$alkyl and t is an integer from 0 to 12.

14. An oligonucleotide in accordance with claim 13 where each of $R_4$ and $R_6$ is independently selected from a group consisting of H, OH and $NH_2$.

15. An oligonucleotide in accordance with claim 14 where the reporter group is biotin or 2,4-dinitrobenzene.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 9
        ( D ) OTHER INFORMATION: /note= "U may be 5-(3- aminoprop-1-yl)-2'deoxyuridine"

( i x ) FEATURE:
        ( A ) NAME/KEY: modified_base
        ( B ) LOCATION: 9
        ( D ) OTHER INFORMATION: /note= "U may be 5-(4- aminobut-1-yl)-2'-deoxyuridine"

( i x ) FEATURE:
        ( A ) NAME/KEY: modified_base
        ( B ) LOCATION: 9
        ( D ) OTHER INFORMATION: /note= "U may be the unmodified deoxyuridine"

( i x ) FEATURE:
        ( A ) NAME/KEY: modified_base (B) LOCATION: 9
                (D) OTHER INFORMATION: /note= "U may be
                    5-(3- iodoacetamidoprop-1-yl)-2'-deoxyuridine"

(ix) FEATURE:
                (A) NAME/KEY: modified_base
                (B) LOCATION: 9
                (D) OTHER INFORMATION: /note= "U may be
                    5-(3-(4- bromobutyramido)prop-1-yl)-2'-deoxyuridin
                    e"

(ix) FEATURE:
                (A) NAME/KEY: modified_base
                (B) LOCATION: 9
                (D) OTHER INFORMATION: /note= "U may be
                    5-(4- iodoacetamidobut-1-yl)-2'-deoxyuridine"

(ix) FEATURE:
                (A) NAME/KEY: modified_base
                (B) LOCATION: 9
                (D) OTHER INFORMATION: /note= "U may be
                    5-(4-(4- bromobutyramido)but-1-yl)-2'-deoxyuridine"

(xi) SEQUENCE DESCRIPTION: SEQ ID NO:1:

CTGGATGTUC CTTC                                                                         14

(2) INFORMATION FOR SEQ ID NO:2:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (xi) SEQUENCE DESCRIPTION: SEQ ID NO:2:

AGACAGCACA GAATTCGAAG GAACATCCAG                                                        30

(2) INFORMATION FOR SEQ ID NO:3:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ix) FEATURE:
                (A) NAME/KEY: modified_base
                (B) LOCATION: 9
                (D) OTHER INFORMATION: /note= "U may be
                    5-[3- (alpha-iodoacetamido)-propyl]-2'-deoxyuridin
                    e"

(ix) FEATURE:
                (A) NAME/KEY: modified_base
                (B) LOCATION: 9
                (D) OTHER INFORMATION: /note= "U may be
                    5-[3- (bromobutyramido)-propyl]-2'-deoxyuridine"

(ix) FEATURE:
                (A) NAME/KEY: modified_base
                (B) LOCATION: 9
                (D) OTHER INFORMATION: /note= "U may be
                    5-[4-alpha- iodoacetamido)-butyl]-2'-deoxyuridine"

(ix) FEATURE:
                (A) NAME/KEY: modified_base
                (B) LOCATION: 9
                (D) OTHER INFORMATION: /note= "U may be
                    5-[4-(4- bromobutyramido)-butyl]-2'-deoxyuridine"

(xi) SEQUENCE DESCRIPTION: SEQ ID NO:3:

CTGGATGTUC CTTC                                                                         14

(2) INFORMATION FOR SEQ ID NO:4:

(i) SEQUENCE CHARACTERISTICS:
  (A) LENGTH: 24 base pairs
  (B) TYPE: nucleic acid
  (C) STRANDEDNESS: single
  (D) TOPOLOGY: linear (xi) SEQUENCE DESCRIPTION: SEQ ID NO:4:

ACCGTCCTTG ACACGATGGA CTCC 24

(2) INFORMATION FOR SEQ ID NO:5:

(i) SEQUENCE CHARACTERISTICS:
  (A) LENGTH: 15 base pairs
  (B) TYPE: nucleic acid
  (C) STRANDEDNESS: single
  (D) TOPOLOGY: linear (ix) FEATURE:
  (A) NAME/KEY: modified_base
  (B) LOCATION: 6
  (D) OTHER INFORMATION: /note= "U may be
       5-[3- (alpha-iodoacetamido)-proply]-2'-deoxyuridine"

(ix) FEATURE:
  (A) NAME/KEY: modified_base
  (B) LOCATION: 6
  (D) OTHER INFORMATION: /note= "U may be
       5-[3-(4- bromobutyramido)-propyl]-2'-deoxyuridine"

(ix) FEATURE:
  (A) NAME/KEY: modified_base
  (B) LOCATION: 6
  (D) OTHER INFORMATION: /note= "U may be
       5-[4- (alpha-iodoacetamido)-butyl]-2'-deoxyuridine"

(ix) FEATURE:
  (A) NAME/KEY: modified_base
  (B) LOCATION: 6
  (D) OTHER INFORMATION: /note= "U may be
       5-[4-(4- bromobutyramido)-butyl]-2'-deoxyuridine"

(xi) SEQUENCE DESCRIPTION: SEQ ID NO:5:

CTCCAUCGTG TCAAG 15